(12) United States Patent
Walsh, Jr. et al.

(10) Patent No.: US 7,289,211 B1
(45) Date of Patent: Oct. 30, 2007

(54) SYSTEM AND METHOD FOR IMAGING SUB-SURFACE POLARIZATION-SENSITIVE MATERIAL STRUCTURES

(76) Inventors: Joseph T. Walsh, Jr., 1310 Washington St., Evanston, IL (US) 60202; Paul Wu, 1580 Sherman Ave., #707, Evanston, IL (US) 60201

( * ) Notice: Subject to any disclaimer, the term of this patent is extended or adjusted under 35 U.S.C. 154(b) by 198 days.

(21) Appl. No.: 11/103,726

(22) Filed: Apr. 11, 2005

Related U.S. Application Data

(60) Provisional application No. 60/561,071, filed on Apr. 9, 2004.

(51) Int. Cl.
   *G01J 4/00* (2006.01)
(52) U.S. Cl. .................................................. 356/369
(58) Field of Classification Search ............... None
   See application file for complete search history.

(56) References Cited

U.S. PATENT DOCUMENTS 5,986,815 A * 11/1999 Bryars ..................... 359/634

7,033,542 B2 * 4/2006 Archibald et al. ....... 422/82.09

* cited by examiner

*Primary Examiner*—Tu T. Nguyen
(74) *Attorney, Agent, or Firm*—Loeb & Loeb, LLP; Jordan A. Sigate

(57) ABSTRACT

A method of visually quantifying a test material along with an imaging apparatus for practicing the method is disclosed. The method comprises: (a) illuminating the test material at a known angle of incidence with diffuse light of a known and adjustable polarization state; (b) receiving light from the test material with a polarization state modified by the test material; (c) measuring an intensity of the polarization components of the received light for each illuminated pixel substantially simultaneously; (d) calculating the Stokes Vector in two dimensions for each illuminated pixel; and (e) creating an image map for the known polarization state. The method may also include adjusting the known polarization or the incident angle of the diffuse light to create additional image maps. The method and apparatus are intended for use in medical imaging including minimally invasive surgery.

20 Claims, 33 Drawing Sheets
(26 of 33 Drawing Sheet(s) Filed in Color)

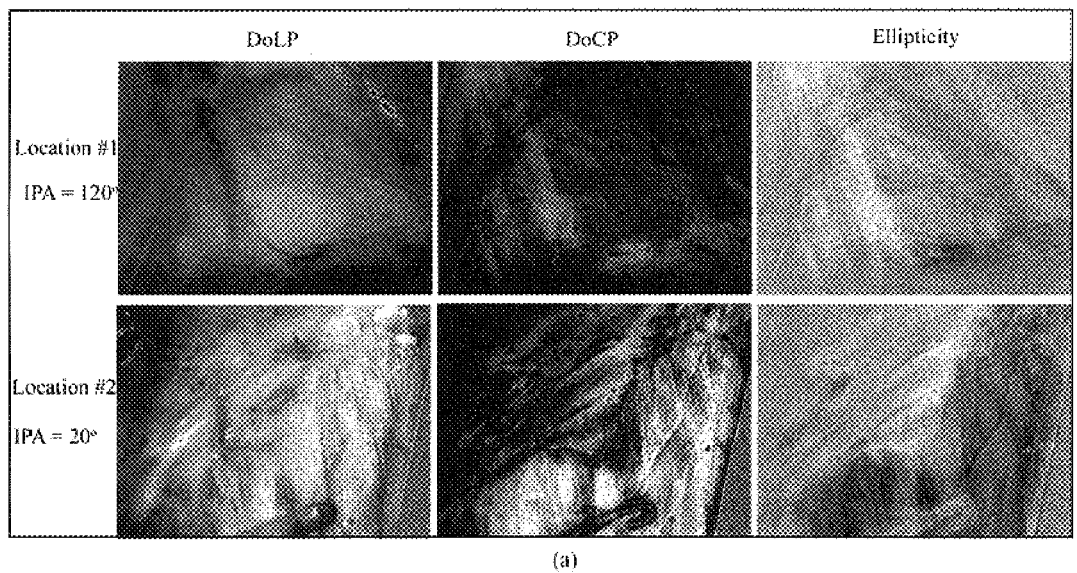
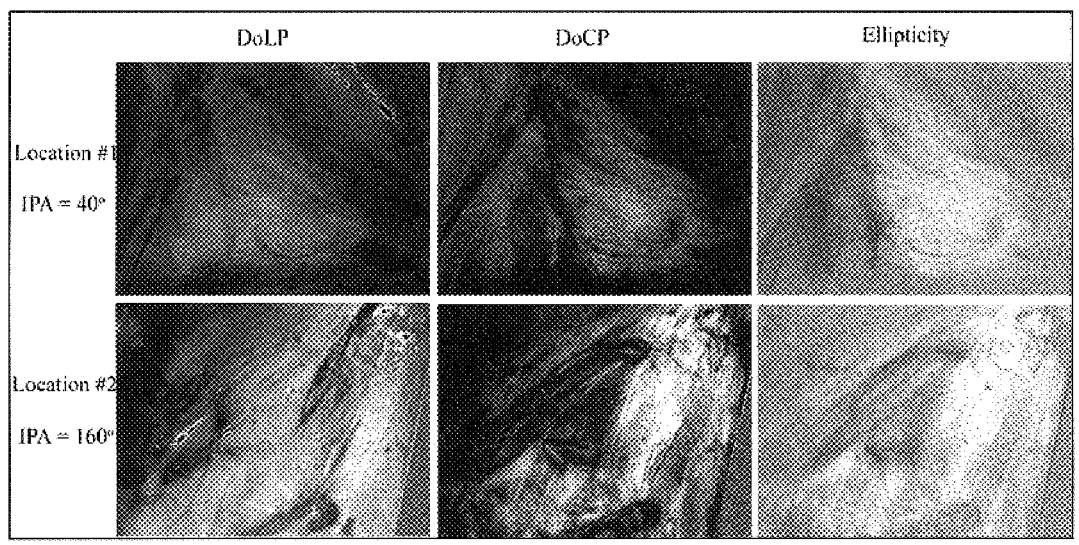
FIG. 28

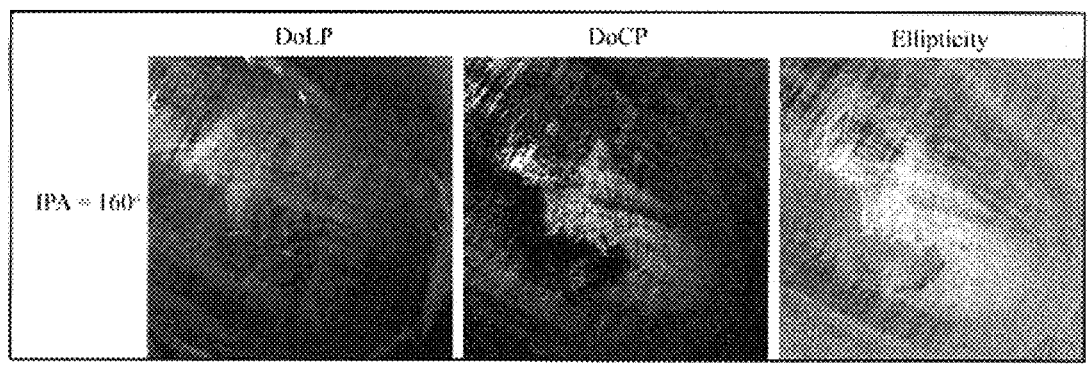
(a)
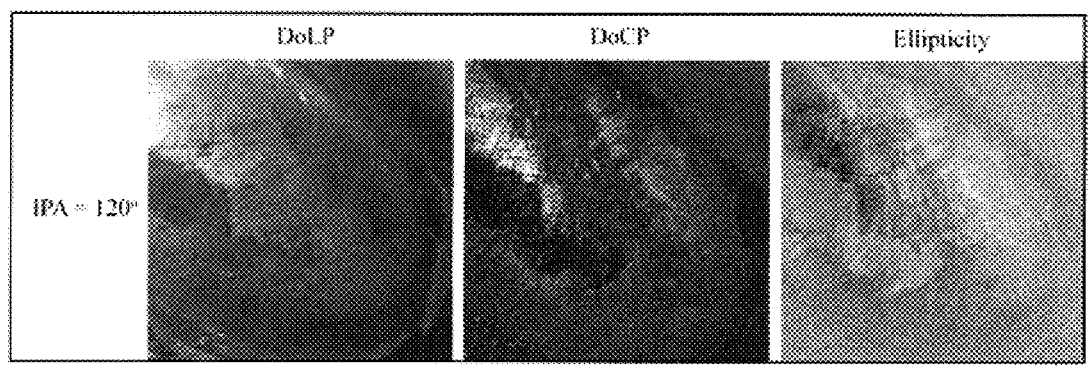
(b)
FIG. 29

SYSTEM AND METHOD FOR IMAGING SUB-SURFACE POLARIZATION-SENSITIVE MATERIAL STRUCTURES

CROSS-REFERENCE TO RELATED APPLICATIONS

This application claims the benefit of the filing date of U.S. Provisional Application No. 60/561,071, entitled "A Method to Image Sub-Surface Polarization-Sensitive Tissue Structures," filed on Apr. 9, 2004, which is incorporated herein by reference.

STATEMENT REGARDING FEDERALLY SPONSORED RESEARCH

The United States government has certain rights to this invention pursuant to Grant No. "R01 HD044015-01A1" from the National Institutes of Health to Northwestern University.

BACKGROUND OF THE INVENTION

1. Field of the Invention

The present invention relates in general to an imaging system and, in particular to an imaging system analyzing the polarization properties of diffuse light with medical applications.

2. Background Art

The identification and characterization of normal and abnormal tissue structures is central to the practice of medicine: diagnosis and guidance of medical and surgical interventions often depend upon knowledge of tissue structure. Optical imaging, whether done with a sophisticated instrument or just by eye, is part of the armamentarium of practicing clinicians who are interested in either diagnosis or treatment of disease. Many patients with various diseases could benefit from improved optical imaging. We provide here significant background on a condition, endometriosis, that has many of the signature aspects of such a disease. The diagnosis and treatment of other conditions, both pathologic and normal, could benefit from the disclosed imaging system and method.

Endometriosis is a disease characterized by the growth of endometrium in regions outside the uterine cavity, usually in the peritoneum. Patients who are symptomatic can exhibit signs and symptoms of pain and infertility making endometriosis the third leading cause of gynecologic hospitalization in the United States.

Current diagnostic techniques have been less adequate in diagnosing endometriosis, including immunologic tests and radiological imaging. Immunologic tests presently lack the sensitivity and specificity for high confidence in endometriosis diagnosis. Ultrasound has also been used to detect endometrial lesions; however, ultrasound lacks the spatial resolution for detection of all but the largest lesions. Magnetic resonance imaging (MRI) has also been used to diagnose endometriosis. MRI is minimally invasive, can image extraperitoneal sites, and detect lesions hidden by dense adhesions. However, MRI is a costly screening tool, and more importantly, the MR contrast between the normal tissue and endometrial lesions is insufficient for accurate diagnosis especially for small lesions. MRI is also presently limited to certain locations at which it could diagnose endometriosis.

Surgical methods for endometriosis have also been used to treat endometriosis. In conservative surgery, apparent endometriosis is located and removed from the peritoneum and associated organs to remove the extrauterine endometrial tissues and restore normal anatomical relations. In definitive surgery, not only is the apparent endometriosis removed but also the ovaries and uterus. A laparotomy can provide a physician direct access to the abdominal area; however, laparoscopy can be less invasive with shorter recovery time and lower costs. Typically, patients who undergo laparotomy require a two- to three-day hospital stay followed by four to six weeks of postoperative recovery. In contrast, patients who undergo laparoscopy usually return home on either the same day or the next day and resume full activities within two to three days after the procedure.

Thus, the current gold standard in diagnosing endometriosis is laparoscopy with tissue biopsy. During this minimally-invasive procedure, the physician locates suspected lesions, which are then biopsied and sent for pathological examination. However, the physician ability to locate lesions is limited. Current laparoscopic equipment limit physicians to assessing tissue characteristics according to color variations in the visible wavelength range. In a conventional laparoscopic imaging system, the major components are the laparoscope, the xenon light source, the three-chip CCD camera, and the display monitor. The laparoscope is a long slender tube comprised of a pathway that passes light from the external xenon source into the peritoneal cavity (or other body cavity) and an optical component barrel that focuses the image back through the length of the scope. The display provides video-rate color images from which the clinical diagnoses are based. Presently, successful diagnoses using conventional laparoscopic imaging depend heavily on the skill of the surgeon to recognize and detect the lesions visually. The difficulty, however, in diagnosing endometriosis during laparoscopy is that the lesions can take on different appearances; in particular the color can vary widely.

In addition, current methods do not allow easy characterization of the deeper, subsurface lesions; often, the confirmation awaits the post-operative analysis of the sample biopsy. The classical implant is a nodular lesion on the peritoneal wall characterized by a variable degree of fibrosis and pigmentation with a color that ranges from blue to brown or black. More vesicular and papular lesions are also common. The depth of the lesion varies from 0 to ~10 mm. The depth of infiltration correlates with pelvic pain; that is, deep implants are highly active in terms of glandular and stromal mitoses, and are often found in patients with pain.

Multiple studies have documented that correlation between visual laparoscopic inspection and histological confirmation of suspected lesions range between 45% and at most 67%. Several studies have reported laparoscopically undetectable lesions by sampling normal-appearing peritoneum in sites common to endometriosis. In these cases, endometriosis was histologically proven to be present in 2% to 66% of the cases. Thus, even after a laparoscopic examination, it is likely that lesions remain undetected and are left intact to cause further pain and infertility.

Thus, there is a need in the industry for an improved imaging technique that will improve the identification of endometriosis lesions. There is an associated need for such imaging technique to work through a laparoscope to minimize patient recovery and improve surgical conditions. There are similar needs in the diagnosis and minimally-invasive treatment of various organs in the human body. Similar needs may be found in the imaging of non-biological materials.

In addition to the imaging techniques mentioned above, techniques involving polarized light have been explored to improve medical imaging. Some prior devices allowed variation of the ellipticity of the incident polarization. However, most of the work focused on the use of crossed polarizers (i.e. the polarizer and the analyzer are crossed such that specularly reflected light is blocked) and parallel polarizers mainly to eliminate specular reflection. This basic technique has been used clinically, for example, to reduce glare during an endoscopic procedure, to enhance the view of vasculature and pigmented lesions in skin, and to image microcirculation through mucous membranes and on the surface of organs.

This concept has also been applied to recent investigations into light scattering spectroscopy. In this technique, the investigators wanted to probe the structure of epithelial cells for precancerous changes using a wide spectrum of wavelengths; however, the penetration depth in tissue for some wavelengths is greater than the epithelial thickness. Using linearly polarized incident light and measuring the two corresponding orthogonal polarization components of scattered light, the intensities of the perpendicular ($I_\perp$) and parallel ($I_\parallel$) components were measured. Hence, the signal that comes from mostly the upper layer of tissue is determined by using subtraction, $I_\parallel - I_\perp$.

Cross-polarization was also used in conjunction with multiple wavelengths and image differencing allowing investigators to detect a deep, highly-scattering subsurface object in tissue, a small piece of absorber in prostate tissue as well as to image subsurface veins, skin surface tissue, and subsurface skin tissue layers. Another technique based on a ratio of the sum and differences of the orthogonal polarization components of the polarizer and analyzer has been used to image superficial layers of the skin. By using a polarization ratio, the resultant images provided contrast that was useful in detecting differences in the superficial layers of various skin conditions. However, to image only light that has propagated within the superficial tissue, one group developed a technique based on image subtraction of collinear, cross-linear, and co-circular detection polarization optics. Their images show the removal of both surface reflected light and multiply-scattered light.

Polarimetry techniques, most notably Mueller matrix polarimetry and Stokes polarimetry, have been applied to a variety of fields such as astronomy and more recently they have also been applied to the biomedical imaging field. Mueller matrix polarimetry relies on arithmetic manipulations of measurements made with formalized combinations of incident polarizations and analyzer types to determine the elements of the Mueller matrix. These combinations rely upon the exclusive use of horizontal, vertical, +45°, −45°, right circular, and left circular polarization states in the polarizer (illuminating) and analyzer (detecting) locations. By shining a collimated laser beam onto a turbid medium and analyzing the diffusely backscattered light, each of the Mueller matrix elements were measured. By using a CCD to capture the backscattered light, sixteen two-dimensional image-patterns resulted and thus allowed the determination of the turbid media properties including average particle size, scattering coefficient, and anisotropy.

Mueller matrix polarimetry can be extended to tissue imaging applications where measurements are made pixel-by-pixel over a region of interest. Thus far, Mueller matrix imaging polarimeters have been used primarily to investigate skin conditions. In these experimental setups, the illuminating and detection optics were not collinear as there was some angle (e.g. 15°) between the two.

In contrast to Mueller matrices, Stokes polarimetry requires formalized combinations of analyzer types but not formalized incident polarizations to determine the elements of the vector. Stokes polarimetry studies in biomedical applications have focused on using narrow coherent beams of light incident on a sample and measuring the degree of linear and circular polarization of the light in transmission mode from the sample. Various techniques have been employed to measure the degree of polarization of laser-speckle fields to determine the time-resolved Stokes vectors of various tissues, and to quantify the degree of polarization of turbid media, tendon, myocardial, arterial and adipose tissue. These techniques cannot image large tissue areas (on the order of several millimeters square) rapidly enough to be a useful diagnostic and surgical tool for in vivo procedures.

In some/most of these prior approaches, the images that are formed from data taken with a scanning beam system, which then must relate the measured optical properties to the point on the material at which the incident, illuminating beam contacts the material. Thus, if light is remitted from the material at a point other than the point of incidence the properties of that remitted light are assigned to the point of incidence. It is believed that such approaches fail to capture at least some highly desirable data.

Consequently, there is a need for an imaging technique that analyzes large tissue areas. There is an associated need for an imaging technique that provides improved imaging rapidly to facilitate surgical procedures.

These and other needs will become apparent to those of skill in the art having the present specification before them.

SUMMARY OF THE DISCLOSURE

The present method and associated imaging apparatus take advantage of two key concepts in tissue optics: the polarization properties of remitted light used as a discriminating factor and radiation that penetrates the tissue sufficiently to image the structures of interest. The present system and method is preferably adjustable to accommodate the polarization properties of tissue structures, thereby allowing visualization of the differences that exist between the tissue matrix of the lesions and the surrounding normal tissue.

The present method and associate imaging apparatus preferably uses a diffuse illuminating light to allow for the simultaneous collection of remitted light from across the entire material surface. The image that is formed from the collected data is based upon the point at which the light is remitted, independent of the point of entry of the illuminating light. Thus, the present system allows for the assignment of image properties based upon the point at which the remitted light leaves the material surface.

The polarization of the incident light in this preferred approach will be controlled and varied while certain polarizations of the detected light will be selected to obtain Stokes vectors. In this way, the Stokes vectors of light remitted from internal tissue structures can be measured pixel-by-pixel thereby obtaining a two-dimensional mapping of, for example, the degree of total polarization, linear polarization, and circular polarization. Differing wavelengths of light may be collected to allow imaging of structures at various depths within the tissue. For example, near-infrared radiation may be collected preferentially—illumination and thus collection of solely near-infrared radiation is not currently done clinically during laparoscopy—to image more deeply within tissue and thus allow detection of deeper lesions.

In particular, there is disclosed a method of visually quantifying a test material (such as biological tissue) using an imaging system. The method comprises: (a) illuminating a portion of the test material at a known angle of incidence with diffuse light of a known and adjustable polarization state; (b) receiving light from the test material, the light having a polarization state modified by the test material; (c) measuring an intensity of the polarization components of the light received from the test material for each illuminated pixel substantially simultaneously; (d) calculate the Stokes Vector (I, Q, U, V) in two dimensions for each illuminated pixel; and (e) creating an image map for the known polarization state with values for each illuminated pixel. The method may also include adjusting the known polarization or the incident angle of the diffuse light and creating additional image maps. The method may further include gathering the saved image maps into a movie.

An imaging system for visually quantifying a test material is also disclosed. The imaging system comprises a light source, optics (e.g. a lens, filter, beam splitter, polarizers, waveplates, and mirrors) operably positioned to receive light remitted by the test material, a plurality of imaging pixels, means for measuring light intensity, calculating the Stokes Vector for each of the imaging pixels and creating an image map. The plurality of imaging pixels may be elements of a CCD camera, CMOS-based imaging system, or similar imaging devices.

The values for the image map are one type of Stokes Vector value selected from the group comprising azimuth, ellipticity, degree of circular polarization (DoCP), degree of linear polarization (DoLP), degree of total polarization (DoTP), the Stokes vector Q, the Stokes vector U, the Stokes vector V, and any combinations thereof.

The light source preferably emits diffuse light of a known polarization state. The states of polarization produced may include elliptical, linear, left-circular and right-circular and any potential combinations thereof. The diffuse light is directed at a known angle of incidence to the test material. The region illuminated by the light can be varied and controlled by adjusting the illumination optics with the goal of using a significant portion of the dynamic range of the optical detection device. The light source is preferably emits at a wavelength that penetrates deeply enough within the tissue to image the structures of interest. For, many structures of interest a near-infrared source is preferable. Among other reasons, near-infrared light penetrates biological tissue more deeply than visible light. The light remitted by the test material has a plurality of constituent waves each having a polarization state modified by the test material.

The optics capture this remitted light and direct it to the plurality of imaging pixels, which are preferably arranged in a 2-dimensional array. The optics may be associated with a minimally invasive medical device selected from the group comprising a laparoscope, a cyctoscope, an ureteroscope, an arthroscope, an endoscope, a dermoscope, or other similar optically based imaging device.

The imaging system may additionally include image map storage, a polarization state controller that varies the polarization state of the diffuse light and a system for changing the angle of incidence to the test material. One of the variably controlled parameters is the incident polarization angle (IPA). Variations in IPA provide a way to probe tissue types that may have a differential response to a certain plane(s) of polarization. The ellipticity of the incident polarization may also be variably controlled so as to intentionally utilize this ability for diagnostic purposes. The imaging system may also include software to display the image maps as either single images or as a movie to assist in diagnostic analysis of the data.

Stokes polarimetry imaging of internal collagenous-based tissues reveals details about tissue structure that are different from those revealed by unpolarized light imaging. Using unpolarized light imaging, the tissues appear rather uniform in texture and color except for the vessels which run throughout the tissue. Using unpolarized near-infrared light, denser tissues (i.e. blood vessels, fat, and muscular abdominal wall) appear lighter in intensity because of the increased backscattering of the light while other less-dense tissues (i.e. peritoneum unattached to the abdominal wall) appear darker as there was less backscattering of light. Still, detailed tissue structural information is lacking in these unpolarized images. Using Stokes-polarimetry imaging, the collagenous fiber-bundle structure running laterally to each other could be visualized. The directionality of these structures and underlying blood vessels are enhanced in the polarization-based image-maps. Hence, the use of polarized light for illumination and in the detection scheme provides an improved approach to visualize sub-surface tissue structures.

One advantage is that large areas of tissue can be scanned to obtain useful structural information without excision or chemical processing.

BRIEF DESCRIPTION OF THE DRAWINGS

The patent or application file contains at least one drawing executed in color. Copies of this patent or patent applicaiton publication with color drawing(s) will be provided by the Office upon request and payment of the necessary fee.

The components in the figures are not necessarily to scale, emphasis instead being placed upon illustrating the principles of the invention. In the figures, like reference numerals designate corresponding parts throughout the different views.

FIGS. 28 and 29 are image-maps of tissues using polarized light and ellipticity values, respectively, for comparison purposes.

DETAILED DESCRIPTION OF THE DRAWINGS

Figure 1:
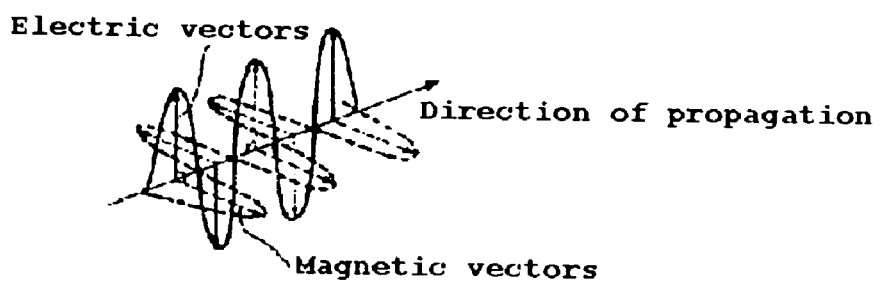
FIG. 1 is a representation of an electromagnetic wave.

While the present invention may be embodied in many different forms, there is shown in the drawings and discussed herein a few specific embodiments with the understanding that the present disclosure is to be considered only as an exemplification of the principles of the invention and is not intended to limit the invention to the embodiments illustrated.

Science of Light

Light is an electromagnetic wave. Electromagnetic waves consist of an electric field and a magnetic field that are always orthogonal to each other and orthogonal to the direction of propagation. By convention, it is the electric field vector that defines the polarization of an electromagnetic wave. The electric field vector can be resolved into orthogonal components, typically x and y components which are labeled $E_x$ and $E_y$. For linearly polarized light, as the wave propagates, the orientation of the electric field remains at a constant angle—that is, $E_x$ and $E_y$ are in phase and have the same amplitude. For circularly polarized light, the orientation of the electric-field vector rotates in either a clockwise or counterclockwise direction, also known as right-circularly or left-circularly polarized light, respectively.

FIG. 1 is a representation of an electromagnetic wave where $E_x$ and $E_y$ have the same amplitude, but one of the components lags the other by a phase difference of $\pi/2$. As a result, the resolved electric-field vector is put in rotational motion as the wave propagates forward. If the phase difference between $E_x$ and $E_y$ is neither 0 nor a multiple of $\pi/2$, then the electric-field vector will be in rotational motion in an elliptical fashion. While strictly all light is elliptical polarized, with circular and linear polarization being subsets of elliptical polarization, it is tradition to use the term elliptical polarization to mean polarization that is neither linear nor circular.

Various optical devices may be used to control the polarization of light. A linear polarizer is a material that allows only light with one orientation to pass. If two linear polarizers are placed in series so that their optical axes are parallel ($\phi=0°$), light passes through both; if the polarization axes are orthogonal ($\phi=90°$), the polarized light from the first is extinguished by the second. As the angle, $\phi$, rotates from 0 to 90°, the intensity of transmitted light decreases. The relationship between polarization angles and transmitted light intensity is given by Malus' Law: $I(\phi)=I(0)\cos^2\phi$, where I=intensity (W/m$^2$). In a polarized light system, the first polarizing element or set of elements constitutes the polarizer and the second element or set of elements constitutes the analyzer.

Similar systems can be designed to create circularly polarized light and measure the intensity of circularly polarized light. But before describing the optical elements used to, for example, create circularly polarized light, we will first explain that the polarization state of light is described mathematically by the Stokes vector. The Stokes vector is a 4×1 matrix consisting of four parameters where I represents the total intensity of the light; Q represents the difference in intensities between the horizontal and vertical linearly polarized components; U represents the difference in intensities between linearly polarized components along the −45° axis with respect to the x-axis and the +45° axis with respect to the x-axis; V represents the difference in intensities between right-circularly and left-circularly polarized light. From each component of the Stokes vector, a degree of polarization can be calculated, where the degree of polarization is defined as the amount of light that is polarized relative to the total amount of light that is both polarized and unpolarized. The three types of degree of polarization measurements that can be determined are:

$$\text{Degree of Linear Polarization} = DoLP = \frac{\sqrt{Q^2+U^2}}{I} \quad \text{(Equation 1)}$$

$$\text{Degree of Circular Polarization} = DoCP = \frac{\sqrt{V^2}}{I} \quad \text{(Equation 2)}$$

$$\text{Degree of Total Polarization} = DoTP = \frac{\sqrt{Q^2+U^2+V^2}}{I} \quad \text{(Equation 3)}$$

A degree of linear or circular polarization value equal to 1 corresponds to completely linear or circular polarized light, respectively. Conversely, a degree of linear or circular polarization value equal to 0 corresponds to light that is not linearly or circularly polarized light, respectively. This does not necessarily mean, however, that the light is unpolarized. Light that registers a DoLP of 0 may be either circular polarized or depolarized. Likewise, light that registers a DoCP of 0 may be either linearly polarized or depolarized. A degree of total polarization value equal to 1 indicates that the light is completely polarized whereas a degree of total polarization equal to 0 indicates that the light is completely depolarized.

Figure 2:
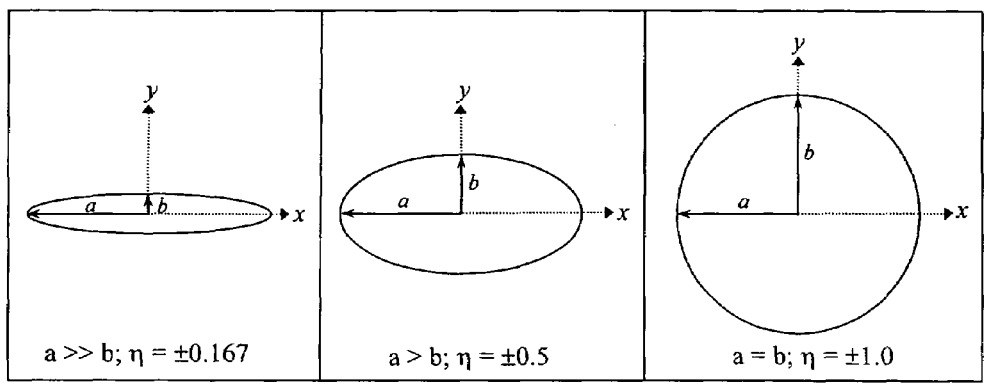
FIG. 2 depicts ellipses with various ellipticities.

Light may also be qualitatively described by its elliptical polarization, for example, how thin or wide the ellipse is. The ellipticity (η) is defined as the ratio of the minor to the major axis of the polarization ellipse; several examples are illustrated in FIG. 2 (b is the length of the minor axis and a the length of the major axis). The sign of the ellipticity value describes the handedness. In particular, a negative value represents light with left-handed rotation, a positive value represents light with right-handed rotation, and zero represents linearly polarized light.

The "V-term" of a light wave describes the difference between right and left circular polarization. Qualitatively, it can be perceived as whether the detected light is closer in form towards a right circular (+1) or left circular (−1) rotation. The ellipticity and the Stokes V-term are closely related. Mathematically, ellipticity can be described in two equivalent forms in terms of Stokes parameters, see Equations 4 and 5.

$$\text{ellipticity} = \frac{V}{I + \sqrt{Q^2 + U^2}} \quad \text{(Equation 4)}$$

$$\text{ellipticity} = \tan\left(\frac{1}{2}\sin^{-1}\frac{V}{I}\right) \quad \text{(Equation 5)}$$

The V-term, present as the numerator in Equation 4 or as the numerator within the trigonometric function of Equation 5, has significant influence on the final value. A plot of $y=\tan(\sin^{-1}(x))$, a function analogous to Equation 5, and its linear fit shows that the $\tan(\sin^{-1}(x))$ curve follows closely to the linear relationship for approximately 90% of the values. Thus, the ellipticity and V-term can be equated to each other by a simple scalar. The regions where the $\tan(\sin^{-1}(x))$ curve strays from the linear fit occur for x-values either above 0.9 or less than −0.9. Image-maps of tissue having a V-value greater than 0.9 or less then −0.9 were very rarely observed. Hence, both ellipticity and V-term image-maps would provide essentially the same qualitative image-map information despite having different numerical scales and ranges of the representative grey levels.

An important property of the Stokes parameters is the property of additivity. If two or more quasi-monochromatic beams propagating in the same direction are superimposed incoherently, the Stokes parameters of the beams can be added and the polarization properties of the combined beam are found by adding the vectors together. When quantifying a Stokes parameter, the actual measurement of irradiance is the sum of the individual beam irradiances. The individual beam irradiances consisted of the individual light packets remitted from the tissue in the backwards direction. The beams that were averaged into the degree of polarization measurements were spatially limited by the size of the detector and the lens.

Through experimentation, it has now been found that Stokes-polarimetry imaging polarimetry of collagenous-based tissues, among other biological tissue and other materials, reveals greater detail about tissue structure than unpolarized light imaging. Hence, the use of polarized light for illumination and in the detection scheme provides an improved approach to visualize tissue structures.

Imaging System and Method

Figure 3:
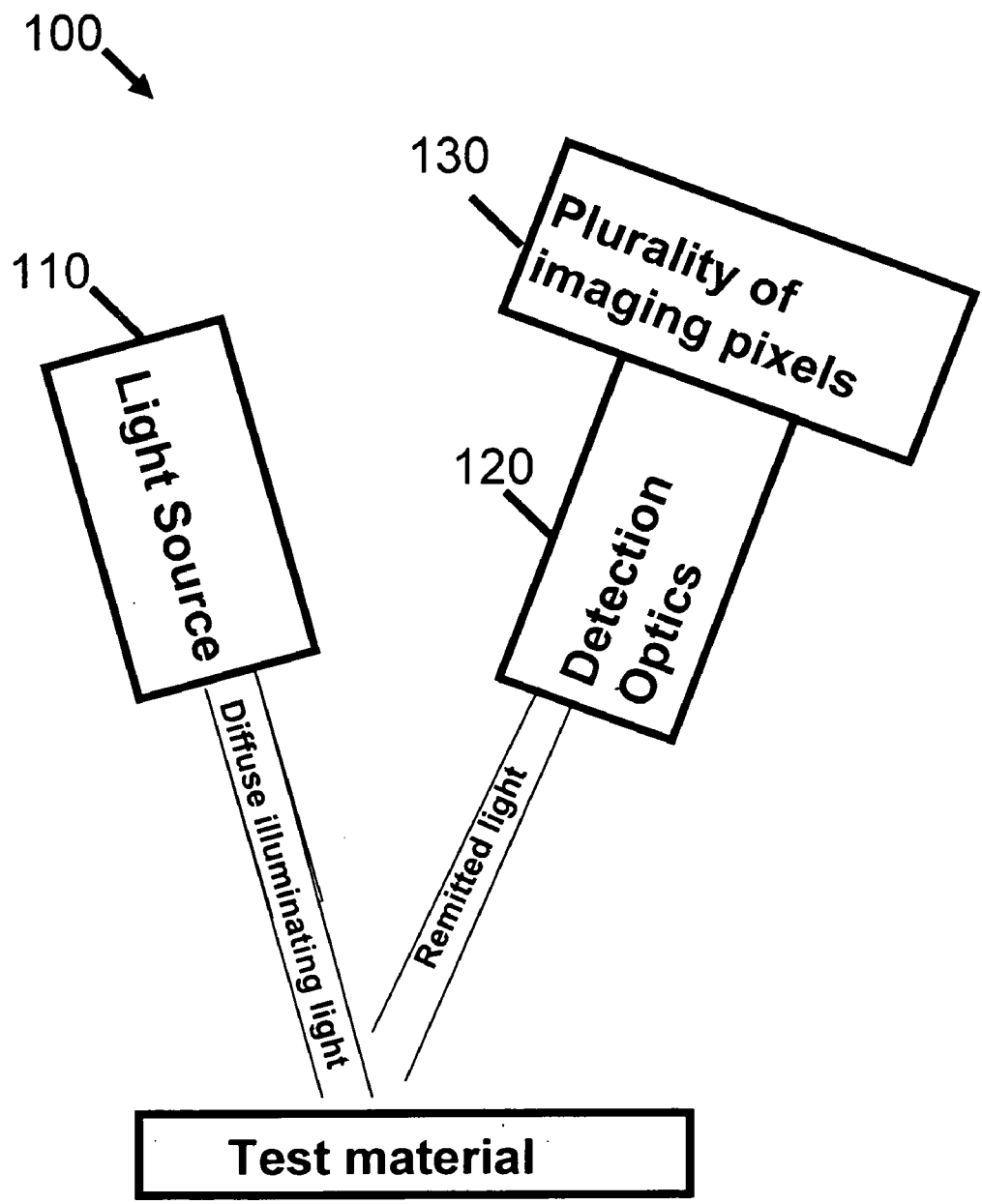
FIG. 3 is a schematic diagram of many of the elements of the imaging system.

As shown in FIG. 3, imaging system 100 comprises a light source 110, optics 120, a plurality of imaging pixels 130, and means for measuring light intensity, calculating the Stokes Vector for each of the imaging pixels and creating an image map. While technically, light is that radiation that we can see, in this disclosure the term light is used more generically to include that radiation that is generally in the range of wavelengths from the UVC to the far-infrared.

The light source 110 preferably emits diffuse light of a known polarization state. Light source 110 may be based around a laser or an incoherent source. In either event, for the imaging of deep tissue structures the light is preferably a near infrared source because, among other potential reasons, near infrared light penetrates biological tissue better than visible light. The light source may be monochromatic or comprised by a plurality of wavelengths. Where the light is composed of multiple wavelengths, the spectroscopic nature of the remitted light could then be sorted out in optics 120 using either filters or by relying upon the RGB-nature of a CCD camera to provide further diagnostic capabilities to the present system and method.

The optical power of the diffuse light may be controlled such that power incident on the tissue can be varied to account for different types of test materials, which have different scattering and absorption properties, such that the remitted light image is within the dynamic range of the plurality of imaging pixels 130, toward minimizing the number of saturated pixels.

The light source 110 may also include a diffuser through which the laser or incoherent light initially passes to remove any random polarization artifacts and more uniformly illuminate the surface with incoherent radiation, which, among other potential benefits, substantially eliminates speckle. The use of a diffuse illuminating light allows simultaneous collection of the remitted light from across the entire test material surface area. Thus, the image that can be formed from the collected data is based upon the point at which the light is remitted, independent of the point of entry of the illuminating light. Thus, the present system allows for the assignment of image properties based upon the point at which the remitted light leaves the material surface.

After passing through the diffuser, the light is then polarized to known polarization state. The states of polarization produced may include elliptical, linear, left-circular and right-circular and any potential combinations thereof. Numerous optical devices, such as waveplates, retarders, and polarizers, exist for the control of polarized light. The resulting diffuse light may be passed through one more rotatable linear polarizers, rotatable quarter-wave plates, and rotatable half-wave plates. For instance, the quarter-wave plates may be Meadowlark Optics AQ-100, AQ-100-840 or AQM-100-840. The polarizing optical devices are move into and out of the light path by a controller to produce a known state of polarization. For instance, incident circularly polarized light was created by properly orienting a quarter-wave plate after the linear polarizer.

In some applications a fiber-coupled laser (Opto Power Corp; Tucson, Ariz.; Model H01-D060-940-FCMS) emitting 940-nm radiation is used. The 940-nm radiation provides relatively deep penetration depth into tissue, which may be desired in some diagnostic situations. In other diagnostic situations other wavelengths and sources of radiation may be more desirable. For instance, the use of near-infrared light in conjunction with medical scopes may present difficulties. For example, laparoscopes inherently have a small aperture (~1 mm in diameter), thus significantly less light passes through the laparoscope lens and reaches the camera than in a benchtop system using a macroscopic lens. Cameras sensitive to visible light usually have much lower near-infrared sensitivity. Hence, the ability to use near-infrared light with a laparoscopic system may require a camera with high sensitivity in the near-infrared range; however, these cameras are rather expensive and their resolution is currently as good as visible-light sensitive cameras.

The laser output is preferably directed through a holographic diffuser (Physical Optics Corporation; Torrance, Calif.; LSDKITCW60-50) and a linear polarizer (Corning; Corning, N.Y.; Polarcor 900H-B2). In one alternative, a glass diffuser (Edmund Optics Tech Spec; Barrington, N.J.; Ground Glass Diffuser 50 mm×50 mm) may be used.

The polarization state of the illumination is varied in several ways: changing the incident polarization angle (IPA) of linearly polarized light and switching between right-circularly or left-circularly polarized light. Light retains polarization information after multiple scattering events; hence, the interaction of light with collagen, a birefringent material, and scatterers within tissue results in remitted light with unique polarization states.

The diffuse light emitted by light source 110 is directed at a known angle of incidence to the test material. This known angle of incidence may be selectively changed by changing the position of the light source 110 either manually or via a controller. This known angle of incidence may also be selectively changed by repositioning the test material. The incident polarization angle (IPA) may also be separately and independently changed to provide a way to probe biological tissue types that may have a differential response to a certain plane(s) of polarization. In other applications, the light may be operably coupled to a wave guide, such as an optical fiber, an articulated arm, or another optical delivery system. For instance, such would be the case with laparoscopic examinations.

The optics 120 are operably positioned to receive light remitted by the test material and direct it to the plurality of imaging pixels 130. The light remitted by the test material has a plurality of constituent waves each having a polarization state modified by the test material. The optics 120 may include a lens, filter, beam splitter, polarizers, waveplates, and mirrors.

A system with fixed incident and detected polarization can be built. In such a case, polarization of the incident light is controlled by a linear polarizer and/or a quarter-wave plate: linear polarized light is achieved by placing a linear polarizer in front of the source; circularly polarized light is achieved by properly orienting a quarter-wave plate after the linear polarizer. However, to acquire the full Stokes vector, a polarimeter is required such that the four elements (I, Q, U, and V) of a Stokes vector can be measured. By varying the retardance and the state of polarization of the light incident on the plurality of imaging pixels 130, these four parameters can be measured. In addition, the total polarization, the linear polarization, and the circular polarization of the light can be determined and used to construct two-dimensional mappings based on these combined parameters. To construct these image-maps, the Stokes vector may be calculated pixel-by-pixel for all the pixels that compose the image-map.

Preferably the detection optics 120 are positioned such that the remitted light traveling within a range of ±1° with respect to the vertical axis is collected. In one example, the remitted light may first pass through a Stokes polarimeter composed of a linear polarizer (Corning; Corning, N.Y.; Polarcor 900H-B2) and a quarter-wave plate (Meadowlark Optics, Frederick, Colo.; AQ-100), each rotated accordingly by motorized rotation stages (Newport Corporation; RV80CC; Irvine, Calif.) to obtain a series of images that would allow the determination of the complete Stokes vector at each pixel.

The optics may also be associated with various minimally-invasive medical devices, for example, a laparoscope, a cyctoscope, an ureteroscope, an arthroscope, an endoscope, a dermoscope, or other similar optically based imaging device.

The plurality of imaging pixels 130 may be elements of a detector, such as a CCD camera or a CMOS imaging system. This allows digital acquisition of the data thus eliminating the introduction of A/D conversion artifacts/errors. The plurality of imaging pixels 130 are preferably arranged in a 2-dimensional array. As the Stokes vector is made up of a series of intensity measurements, one feature of the pixels necessary for analysis of the detected light is the relationship between the intensity of light incident on the pixels and the digital read-out values from the pixel. By knowing the nature of the relationship, it can be determined whether read-out values proportionately represent intensity levels of light incident on the pixels. Moreover, for a Stokes-polarimetry imaging system, the detector (plurality of pixels) and optics 120 should be insensitive to polarization since the technique is based on precise intensity measurements independent of polarization state. The polarization state detected should be governed by the Stokes polarimeter and not be influenced by the polarization sensitivity of the pixels and imaging optics.

The detector preferably meets several other criteria: near-infrared sensitivity; frame rates≧30 frames/s (fps); progressive non-interlaced and full-pixel readout; synchronizable with external trigger; digital output and control; and sufficient bit resolution. With a greater bit resolution, finer intensity measurements can be made. Bit resolution should be greater than 8 bits with the understanding that the cost of the detector increases along with bit resolution.

If the detector has near-infrared sensitivity, it provides the ability to detect light with wavelengths that the human eye or conventional cameras are not sensitive to. The advantage of using near-infrared light in imaging tissue is that near-infrared light penetrates deeper into tissue than visible light. However, the present system does not require the use of near-infrared light. Additional illumination wavelengths in the visible range could also be incorporated into the imaging system. Besides the added spectroscopic component that could yield depth and chromophore information in tissue, the selection of visible wavelengths permits the use of cameras sensitive in the visible region. Currently, visible wavelength cameras have higher resolution, higher sensitivity, and greater dynamic range than near-infrared cameras. The higher resolution and greater dynamic range will improve the analysis of suspicious tissue regions in image-maps while the higher sensitivity will permit earlier integration with medical scopes. The constant advancement in imaging chip technology will lead to greater improvements in optical imaging and favorable economies of scale.

Frame rates on par with or greater than standard video rates facilitate the acquisition of images rapidly in succession. Because constructing degree of polarization image-maps require several intensity images, higher frame rates are preferable. In essence, the detector should not be the limiting factor in terms of how fast data can be collected.

All pixel values are preferably read at substantially the same instant. This allows measurement of light from an instantaneous capture rather than over a series of captures where alternate rows/columns are acquired. It is preferable that the detector allows image acquisition to be coordinated with external events. For example, after an optical component has been rotated to a certain angle, a signal can be sent to trigger the detector. Digital control simplifies remote operation of the detector with a PC.

In a preferred embodiment, a camera lens (Canon; Japan; 100 mm f/16) focuses the remitted light from the detection optics 120 onto a visible-NIR sensitive CCD (Hitachi; Japan; KP-F120CL; 10-bit resolution, 1392×1040 pixels). This CCD exhibits linearity over its entire dynamic range.

In some examples, the incident polarization used may be linearly polarized light while a degree of linear polarization (DoLP), degree of circular polarization (DoCP), or any other polarization-based metric is the image-map created. One way to achieve this analysis involves having the linear polarizer in the optical train at the illumination end rotated such that the polarizer axis changes the IPA.

In other examples, the incident polarization used may be circularly polarized light while a degree of linear polarization (DOLP) or degree of circular polarization (DoCP), or any other polarization-based metric is the image-map created. One way to achieve this analysis involves placing an additional quarter-wave plate (optical retarder) after the linear polarizer in the optical train at the illumination end such that the fast axis of the quarter-wave plate is +45° or −45° offset from the linear polarizer axis.

Further, different ellipticities of incident polarization may be used while a DoCP, DoLP, or any other polarization-based metric is created. One way to achieve this analysis involves an additional quarter-wave plate (optical retarder) placed after the linear polarizer in the optical train at the illumination end such that the fast axis of the quarter-wave plate can be rotated with respect to the linear polarizer axis. One skilled in the art would recognize that in lieu of quarter-wave plates and polarizers, other polarization optics including fast polarization modulation optics (e.g. photoelastic modulators, liquid crystal variable retarders) could be used in the polarization generator and in the Stokes polarimeter.

Images may be transferred from the plurality of imaging pixels 130 to a processing system 200 via an image acquisition card. In one approach, the processing system 200 may be a general purpose computer system (e.g., Dell Precision Workstation 530; Round Rock, Tex.) and the image acquisition card may be a PCI-1428 from National Instruments; Austin, Tex. Image processing and analysis may be carried out on this processing system using IDL v5.6 (Research Systems Inc.; Boulder, Colo.) and Vision Builder v6.1 (National Instruments; Austin, Tex.).

Data may be collected systematically for each of a plurality of incident polarization angle and various orientations of the test material. To construct degree of polarization image-maps at a specific incident polarization angle and specific target tissue orientations, images may be acquired with a plurality of settings.

Figure 5:
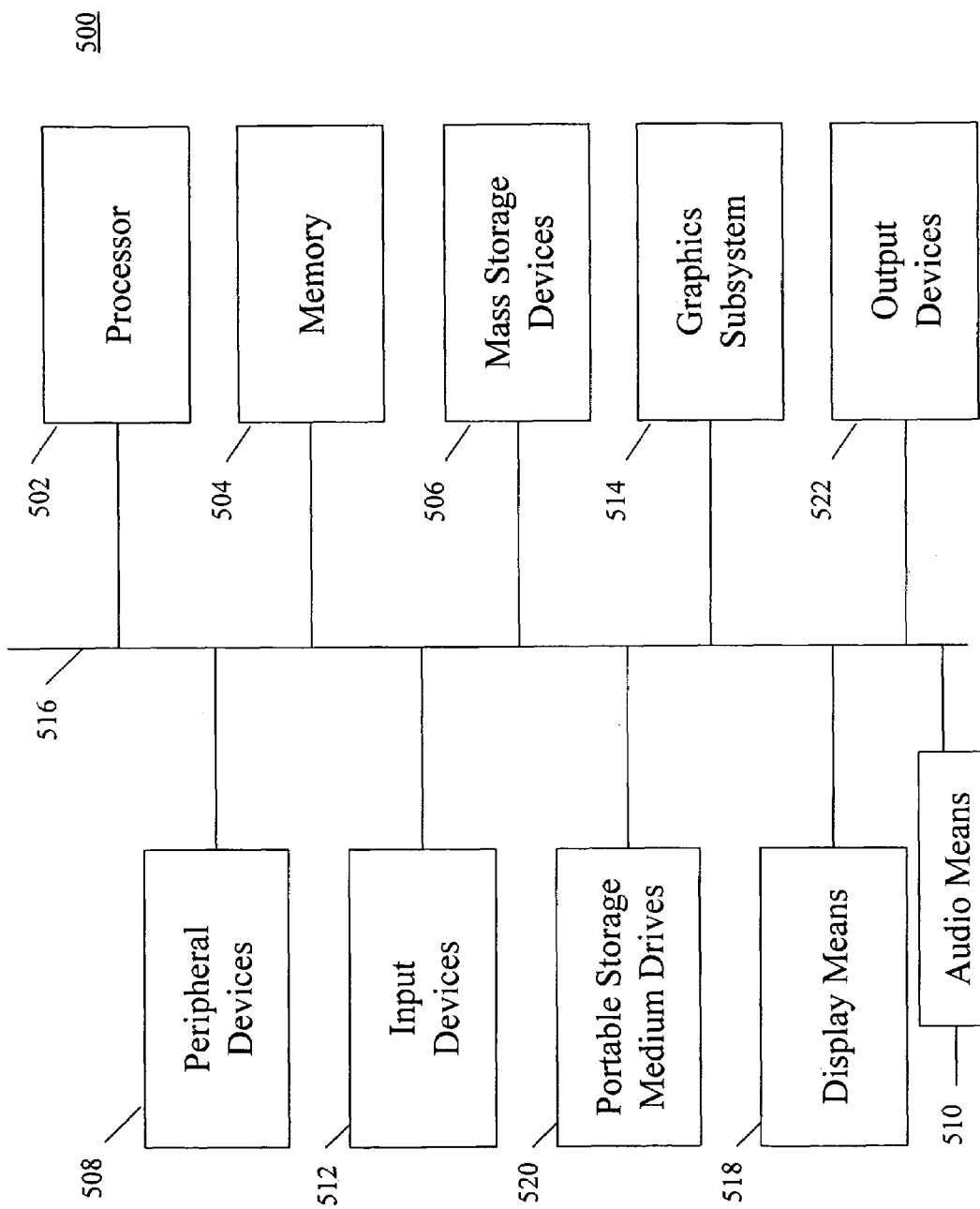
FIG. 5 is a block diagram of a processing system.

FIG. 5 illustrates a high-level block diagram of a general purpose computer system which is used, in one embodiment, to implement the processing system for the method and system of the present invention. The general purpose computer 500 includes a processor 502 and memory 504. The processor 502 may contain a single microprocessor, or may contain a plurality of microprocessors. Memory 504 stores, in part, instructions and data for execution by processor 502. If the system of the present invention is wholly or partially implemented in software, including computer instructions, memory 504 stores the executable code when in operation. Memory 504 may include banks of dynamic random access memory (DRAM) as well as high speed cache memory. The general purpose computer 500 further includes a mass storage device 506.

The general purpose computer 500 may also include peripheral device(s) 508, audio means 510, input device(s) 512, portable storage medium drive(s) 520, a graphics subsystem 514, and a display means 518. For purposes of simplicity, the components shown in FIG. 5 are depicted as being connected via a single bus 516. However, the components may be connected through one or more buses, which may also include external data communication means (e.g., Internet, Intranet, etc.). For example, processor 502 and memory 504 may be connected via a local microprocessor bus, and the mass storage device 506, peripheral device(s) 508, portable storage medium drive(s) 520, and graphics subsystem 514 may be connected via one or more input/output (I/O) buses. Mass storage device 506, which is typically implemented with a magnetic disk drive or an optical disk drive, is in one embodiment, a non-volatile storage device for storing data and instructions for use by processor 502. In another embodiment, mass storage device 506 stores the components of the server 38. In another embodiment, the storage device may also be the mass storage device 506. The computer instructions that implement the method of the present invention also may be stored in processor 502.

Portable storage medium drive 520 operates in conjunction with a portable non-volatile storage medium, such as a floppy disk, or other computer-readable medium, to input and output data and code to and from the computer system of FIG. 5. In one embodiment, the method of the present invention that is implemented using computer instructions is stored on such a portable medium, and is input to the computer system 500 via the portable storage medium drive 520. Peripheral device(s) 508 may include any type of computer support device, such as an input/output (I/O) interface, to add additional functionality to the computer system 500. For example, peripheral device(s) 508 may include a network interface card for interfacing computer system 500 to a network, a modem, and the like.

Input device(s) 512 provide a portion of a user interface. Input device(s) 512 may include an alpha-numeric keypad for inputting alpha-numeric and other key information, or a pointing device, such as a mouse, a trackball, stylus or cursor direction keys. In order to display textual and graphical information, the computer 500 of FIG. 5 includes graphics subsystem 514 and display means 518. Display means 518 may include a cathode ray tube (CRT) display, liquid crystal display (LCD), other suitable display devices, or means for displaying. Graphics subsystem 514 receives textual and graphical information and processes the information for output to display 518. Additionally, the computer of FIG. 5 includes output devices 522. Examples of suitable output devices include printers, and the like.

The devices contained in the computer system of FIG. 5 are those typically found in general purpose computers, and are intended to represent a broad category of such computer components that are well known in the art. The system of FIG. 5 illustrates one platform which can be used for practically implementing the method of the present invention.

The Stokes vector, [I Q U V], is calculated pixel-by-pixel from the acquired images to ultimately create an image map. The values for the image map are one type of Stokes Vector value selected from the group comprising azimuth, ellipticity, eccentricity, DoCP, DoLP, DoTP, the Stokes vector Q, the Stokes vector U, the Stokes vector V, and any combinations thereof.

Processing may be performed on the light images to calculate ellipticity values over a two-dimensional space by using the Stokes parameters and Equations 4 or 5. Ellipticity values range between −1 and +1. The ellipticity maps may be displayed using 256 gray levels, where ellipticity value of 0 can be centered at level 128. By examining the histogram of the ellipticity maps, the ellipticity values can be manually or automatically scaled so as to maximize the displayed dynamic range (for a typical 8-bit display, 0 to 255); such scaling can also be done for the display of other image maps.

Additional details about tissues composed primarily of irregularly organized, multidirectional collagenous or smooth-muscle bundles can be elicited from ellipticity (or nearly equivalently the V-term) image-maps. While DoLP and DoCP measurements range from 0 to 1, ellipticity measurements range from −1 to 1. This range and more notably the inclusion of the negative range permit differentiation of the helicity of remitted light. Although neighboring tissue structures and localized regions may remit light with very similar degrees of polarization, the helicities can be significantly different. These helicity differences depend on the refractive indices within the tissue which accordingly affect the sign and amount of phase. Thus, the utilization of ellipticity (or V-term) image-maps provide greater contrast among tissue variations at selected IPAs even if DoLP and DoCP image-maps show indistinguishable features.

For some IPAs and some test materials, displaying ellipticity or V-term image-maps will provide visual enhancement of biological tissue structural features when compared to DoLP or DoCP image-maps. At other IPAs for some test materials, the ellipticity and V-term image-maps will be on-par with DoLP and DoCP image-maps in terms of observable bundle structures. Although ellipticity and V-term image-maps could be used for any tissue type, the analysis of a variety of internal tissues indicated that these metrics were better suited for tissue structures with less-ordered structures, for example, the multi-directional fiber-bundles within the broad ligament and the distended bladder, whereas the DoLP and DoCP image-maps sometimes lacked sufficient contrast to differentiate tissue structures. In the broad ligament, the collagenous structures appeared without texture, and in the distended bladder, the bundles of smooth muscle were not clearly observed. Tissue samples illuminated with polarized light set at certain IPAs and the construction of image-maps with ellipticity measurements resulted in the display of tissue variations that were finer than those displayed in either DoLP or DoCP image-maps. Compare FIGS. 28(*a*) and 29(*a*) with FIGS. 28(*b*) and 29(*b*). For other tissue types, such as the peritoneum or the small intestine, the ellipticity image-maps provided information similar to that provided by DoCP image-maps.

Figure 30:
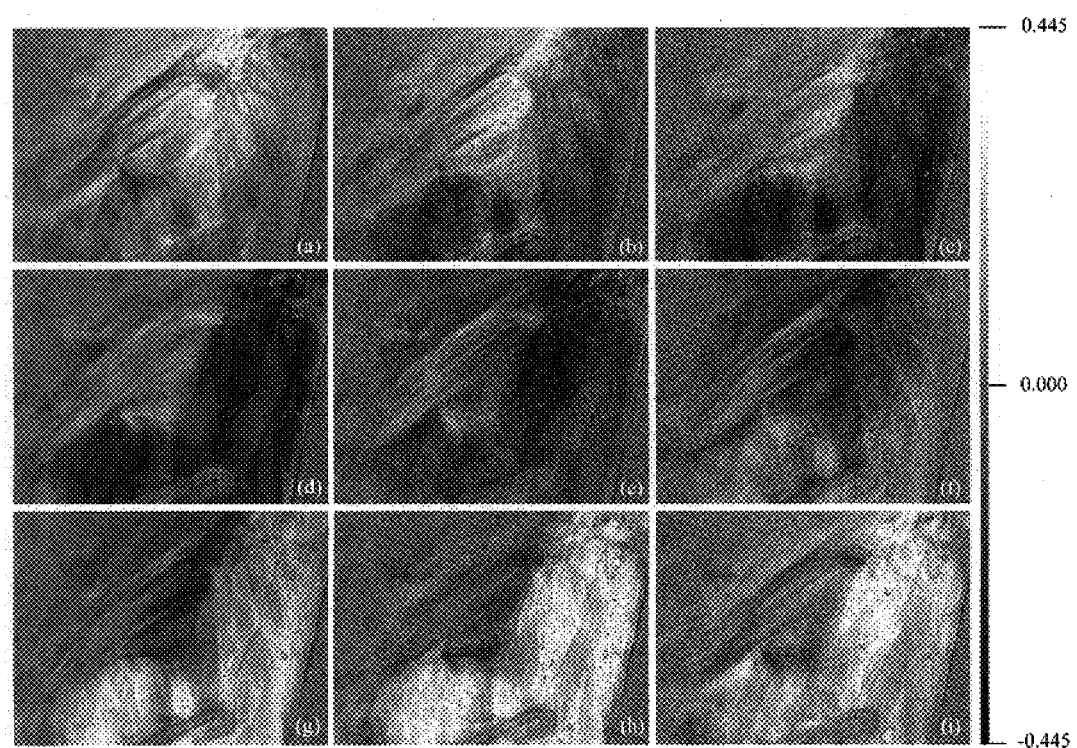
FIGS. 30-32 are a series of image-maps that could be viewed in a movie loop.
Figure 31:
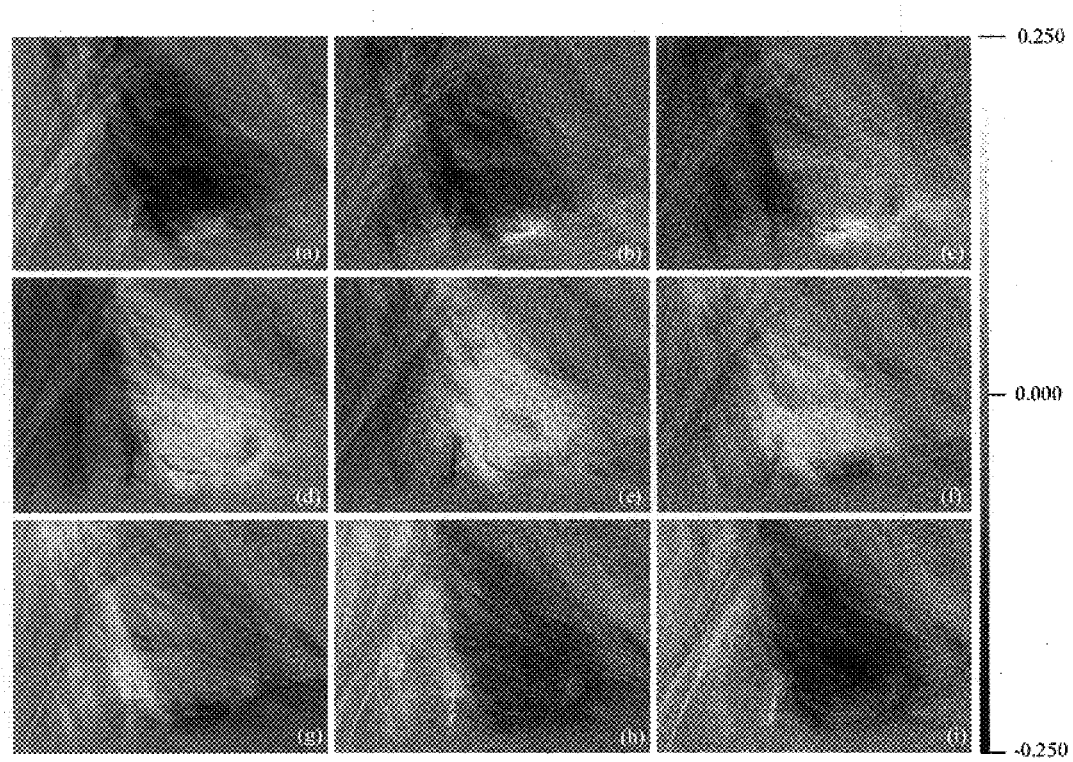
Figure 32:
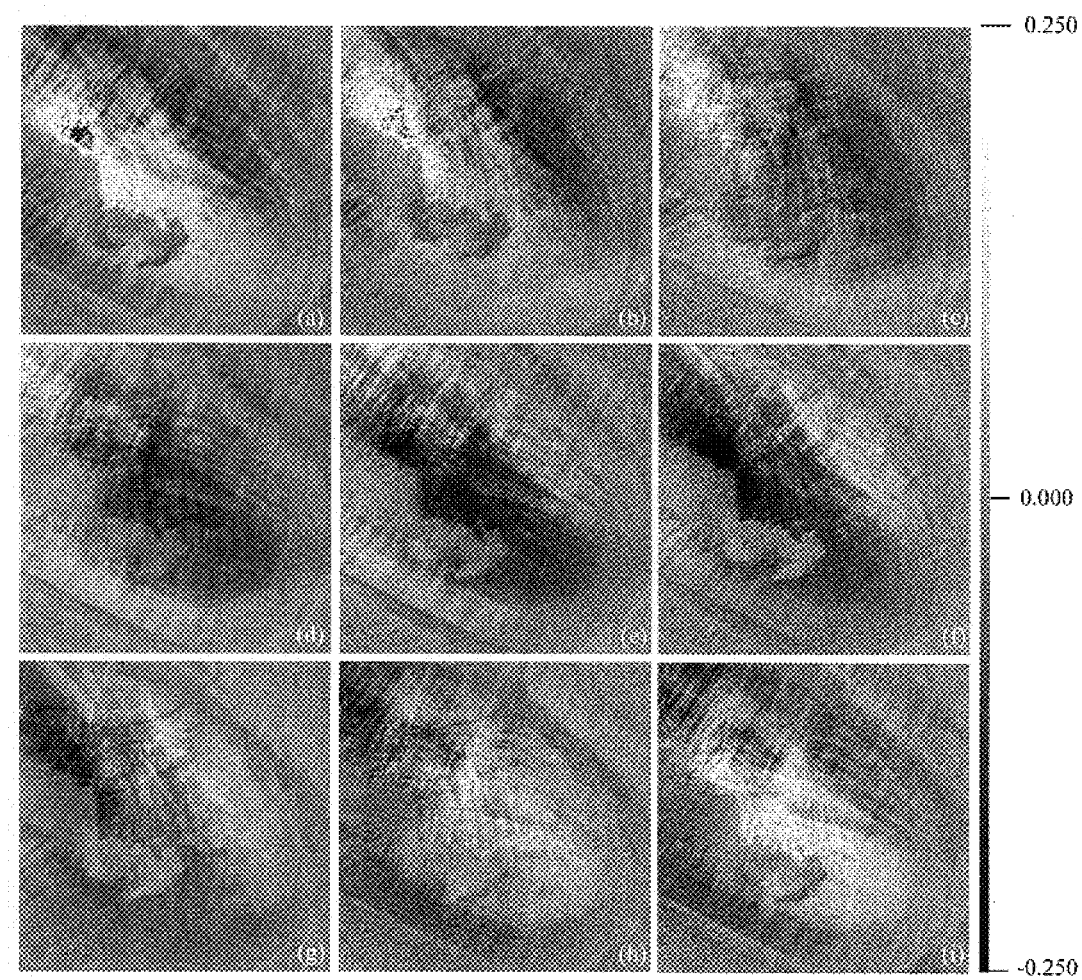

The ellipticity or V-term values of remitted light from the tissue also exhibit a dependence on the incident polarization. As the linear bundle structures took on certain alignments within the field-of-view, the ellipticity or V-term image-maps provided greater detail in these localized regions when an optimal IPA is used. Although there was not one IPA that could be considered optimal for all regions of the tissue, viewing the images in a playback loop (or movie) provides diagnostic information about tissue structure as in FIGS. 30-32, the fine details over the entire field-of-view can be visualized and a more complete picture of the make-up of the tissue is achieved.

Figure 33:
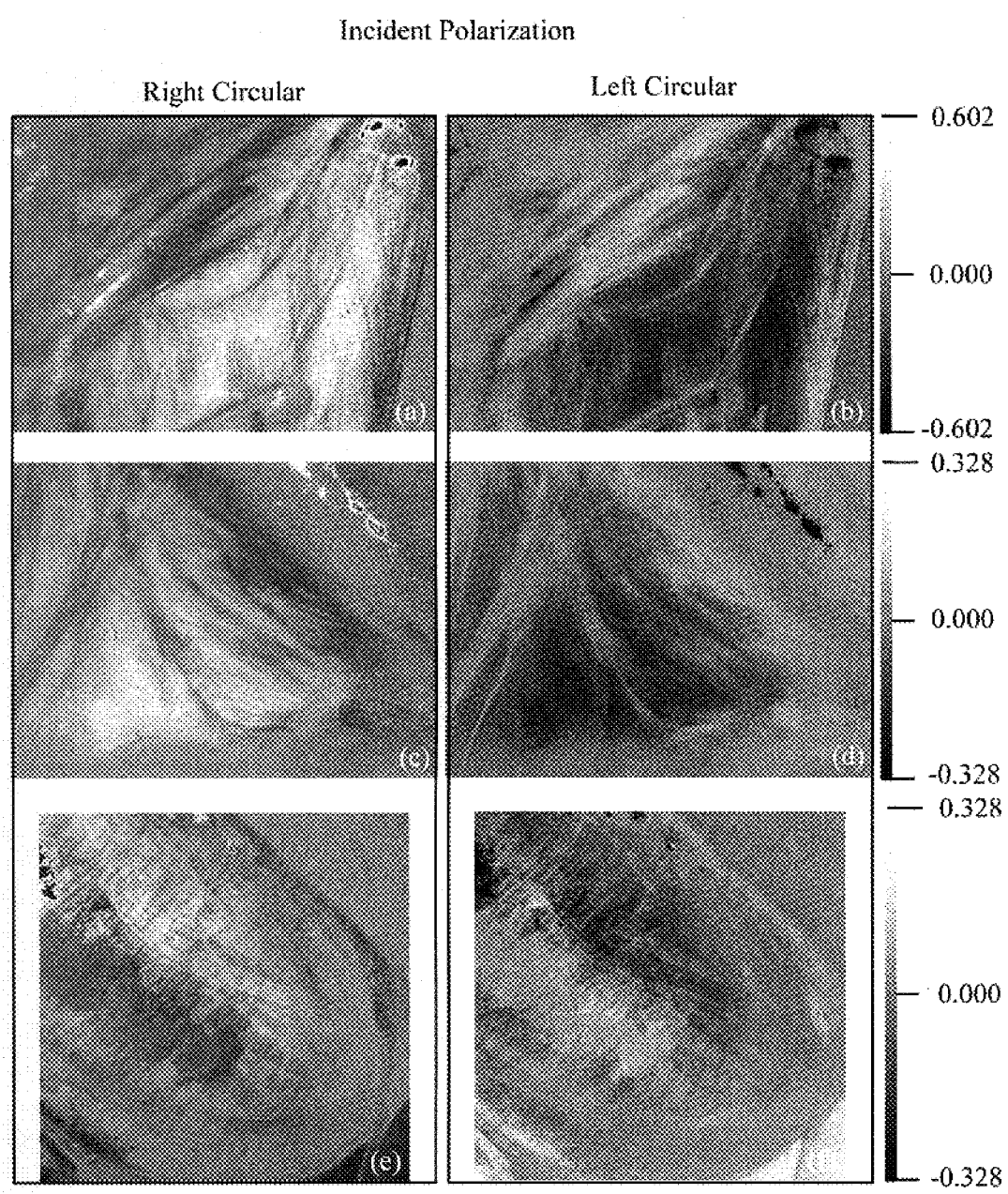
FIG. 33 shows the difference in image maps facilitated by circular polarization.

In FIG. 33, the use of right-circularly or left-circularly polarized illumination resulted in ellipticity image-maps that differed from those created with linearly polarized light. These image-maps showed unique tissue structures that were sensitive to circularly polarized light. Besides the high level of tissue structural detail, one interesting feature to note is that the grey-levels in the image-map produced with one helicity of circularly polarized light appeared inverted when the other helicity was utilized. Hence, the use of either left-circular or right-circular incident polarization caused reversal of the remitted light helicities, but did not change the elliptical shape of the remitted light.

The use of incident circular polarization may provide an alternative view of the test material or tissue. Because circularly polarized light interacted with tissue differently than linearly polarized light, the image-maps showed unique features, see FIG. 33. By specifying the helicity of incident circular polarization, locations where the incident helical direction is preserved, reversed, or converted to linear form are indicated on the image-maps. The similarities between the image-maps formed with either right-circular or left-circular polarization, despite the inversion of grey-levels, indicate no effective preferential polarization properties (i.e. circular diattenuation or retardance) attributable to helicity direction.

The use of different wavelengths of illuminating light may provide additional information from various depths of tissue. In addition, tissue chromophores, particularly blood, have specific absorption bands; thus processing of data created with different color light will yield information about chromophore distribution that may be polarization-sensitive. The wavelength dependence can be obtained in several ways: 1) illuminate sequentially with single colors and collect each color image separately; or 2) illuminate with and collect broadband light and separate the colors either during detection or, in some cases equivalently, during processing. Algorithms may also be used to combine information gained from multiple-wavelengths and form a spectroscopic polarization-based image-map.

In a preferred approach, the polarization-based image-maps may be presented graphically. In this approach, a standard color look-up table (Fire; ImageJ, National Institutes of Health, USA) was applied to the image-maps to show the different levels of polarization. The histograms of the image-maps may be expanded without loss of relevant data so the levels would make the best use of the color look-up table and display with sufficient contrast.

The image-maps may be displayed on a video monitor, for example, as a total of 9 (in a 3×3 collage) or in a sequence (i.e. a movie), which may be more helpful in discerning tissue structural features.

The processing system 200 may additionally include image map storage, a polarization state controller that varies the polarization state of the diffuse light and a system for changing the angle of known angle of incidence to the test material.

Figure 6:
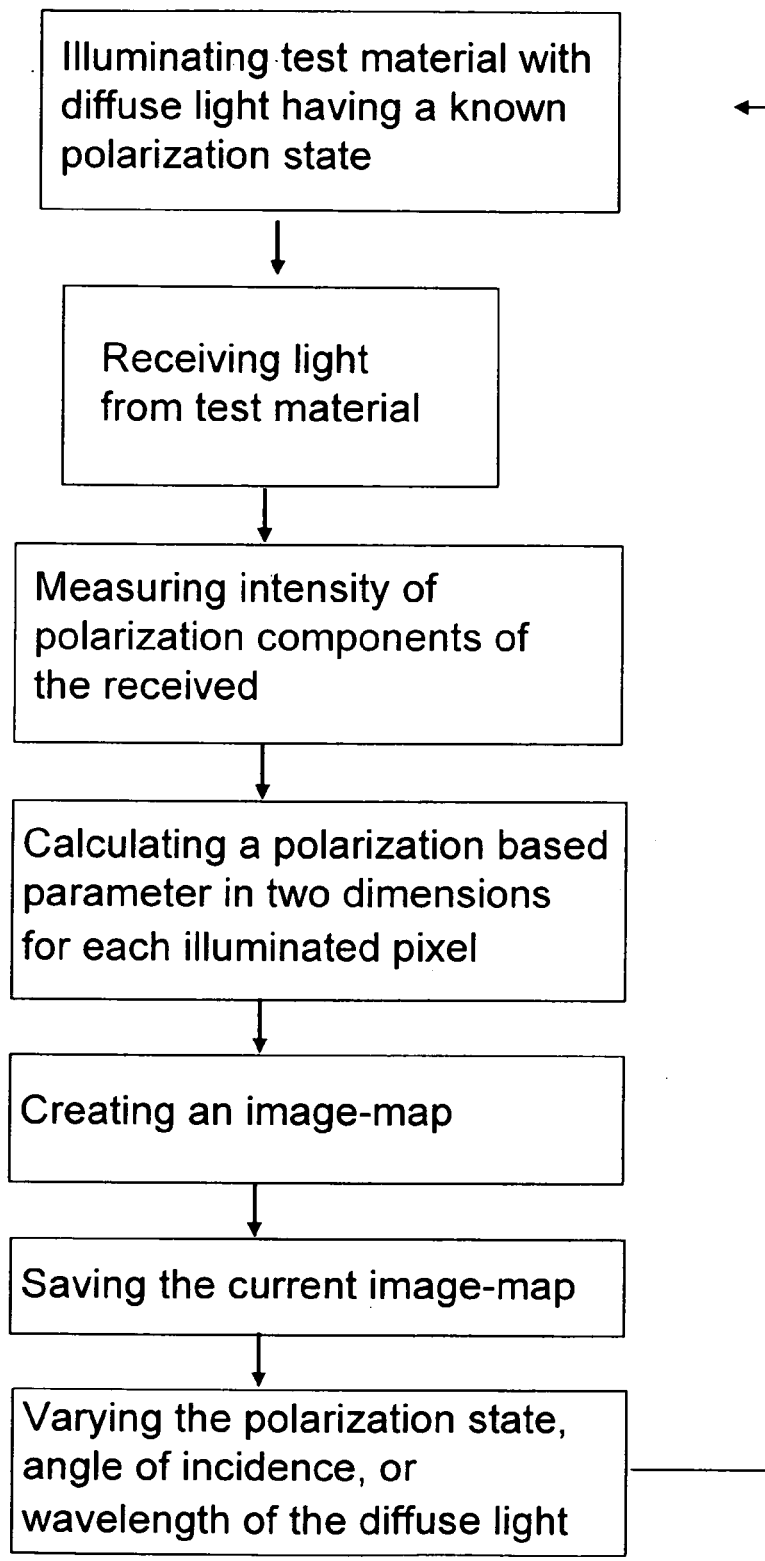
FIG. 6 is a flow diagram of the present method.

The apparatus is used in performing a method of visually quantifying test material, such a biological material and other materials. The method is depicted in FIG. 6. At its most basic, the method includes: (a) illuminating a portion of the test material at a known angle of incidence with diffuse light of a known and adjustable polarization state; (b) receiving light from the test material, the light having a polarization state modified by the test material; (c) measuring an intensity of the polarization components of the light received from the test material for each illuminated pixel substantially simultaneously; (d) calculating the Stokes Vector (I, Q, U, V) in two dimensions for each illuminated pixel; and (e) creating an image map for the known and adjustable polarization state with values for each illuminated pixel. The values for the image map are one type of Stokes Vector value selected from the group comprising azimuth, ellipticity, eccentricity, degree of circular polarization (DoCP), degree of linear polarization (DoLP), degree of total polarization (DoTP), the Stokes vector Q, the Stokes vector U, the Stokes vector V, and any combinations thereof.

In many instances, the image map is saved; one parameter of the polarization state parameters is varied and the method is repeated for this new polarization state. The change in the polarization state may be accomplished by changes in the light source or by moving the test material. This saving of image maps and variation of the polarization state continues until all of the polarizations are completed. Similarly, there are instances, for example, where varying the angle of incidence may provide desirable data. In those instance, the angle is varied and image maps saved. In another example, the wavelength of the light may be changed and additional image maps saved. Of course, as would be understood by those of skill in the art the variations of these and other systemic variables may be selectively combined to provide further detail regarding the test material. In one approach, the saved image maps may be fashioned into a movie to provide another dimension to the data being reviewed.

Discussion of Various Biological Tissue Applications

The test material can be biological tissue that may have normal or pathologic variations in its structure, for example, there may be variations in the tissue's birefringent properties. In particular, the biological tissue may be skin, part of the GI track, part of the urinary track, along the reproductive track, along the respiratory track, part of a peritoneal wall, part of a pelvic organ (e.g. uterus, prostate, bladder), part of an abdominal organ (e.g. gall bladder, kidney, liver, small intestine, large intestine), or part of the nervous system. The biological tissue may have blood vessels or nerves.

Polarization angles that are parallel to either index of refraction axis in a birefringent structure allow the light to maintain its initial polarization state. Polarization angles that are oblique to either index of refraction axis changes the polarization state. Depending on the angle between the plane of wave vibration and the indices of refraction, phase is added or subtracted into the wave and some form of elliptically polarized light results. When circularly polarized light interacts with a birefringent material such as collagen, the birefringence also affects the polarization properties of remitted light. Collagen is unique in that it is strongly birefringent which provides birefringence effects on the polarization-based imaging of tissue.

Phase can be added to or subtracted from the circularly polarized wave transforming it into a more linear form. The interaction of polarized light with tissue and the propagation of light in tissue involves multiple scattering events. Purely reflected light or glare maintains its initial polarization, but multiply scattered light carries polarization information about the tissue dependent upon interactions it had with multiple scatterers and materials that alter the polarization state of light. As indicated in the literature, the preservation of polarization does occur after many scattering events.

Both the peritoneum and broad ligament are primarily collagen based, but each has a different structure-function relationship with surrounding tissues. Briefly, the peritoneum is a serous membrane comprised of loose bundles of connective tissue interlaced in a plane parallel to the peritoneal surface. The peritoneum lines the abdomen and reflects over the contained viscera. The broad ligaments are bilateral folds of the abdominal and pelvic peritoneum enclosing connective tissue and providing support for the ovaries.

In the peritoneum and broad ligament, some of the collagen fibers are organized into bundles. There is a strong correlation between the orientations of the collagen and the functional requirements of the tissue. For example, if the distribution of the fiber orientation is anisotropic, the stress across the tissue is normally in a predominant direction. Further, if the fiber orientation is arranged isotropically, the stress across the tissue is normally in multiple directions. Although the orientation of collagen fibers can be studied on many scales, from microscopic to SEM levels, in this study, the Stokes-polarimetry imaging system took images on a millimeter scale. On this scale, the aggregates of collagen bundles that contributed to the major structural components of the tissue could be identified. The minority of isotropic-distributed and randomly-oriented collagen fibers did not significantly affect the overall polarization signal at this scale. Correspondingly, the image-maps of abdominal peritoneum show the fiber-bundles arranged in a regular pattern and pointed in a general direction. In the body, the abdominal peritoneum is relatively fixed and lies flat against the abdominal wall although movements of the abdominal wall may distort it slightly.

In contrast, the alignment of fiber-bundles in the broad ligament is less regular. The large bundles occur with different orientations and in a more random structure. These bundles are commonly separated by large structureless areas. As one of the functions of the broad ligament is to suspend the ovaries, the collagen bundles providing this additional support could be observed in the image-maps. Another location on the broad ligament immediately lateral to the uterus had little structural requirements; hence the image-maps showed little definition in the collagen bundles. As the collagen bundles were less organized, the polarization properties of remitted light were significantly scrambled since refraction indices of the collagen fibers were not regular.

Although tissues/organs such as the gall bladder, bladder, uterus, and small intestine that exist in the internal abdominal cavity are comprised primarily of smooth muscle walls, they too each have polarization-sensitive constituents that cause uniquely polarized light to be remitted. Small intestine Stokes polarimetry image-maps generated by the present system and method reveal the nerves that run around the intestinal wall indicating the feasibility of imaging nerves on prostates and other structures during surgeries.

The tissue orientation angle and geometry of the tissue with respect to the polarized light source contribute to the polarization changes of remitted light. One must recognize that the polarization of remitted light is not only influenced by the superficial tissue layers but also by the underlying tissue layers. Hence, this imaging technique may provide utility in subsurface tissue imaging. Scars, keloids, hypertrophic scars, and stria all have organizations of collagen fibers that are different from normal skin. For example, during the healing process of cutaneous wounds, many changes occur at the wound site. Because the strength of the tissue repair is primarily determined by collagen, it may be of interest to monitor changes. Early in the repair phase, collagen bundles are much narrower than normal. There is also a more disorganized structure at the molecular or small-fibril level and a loss of birefringence. As healing progresses, the fibril diameter increases and fibers become more compact. Scar collagen differs significantly from the bundles and organized pattern of normal dermal collagen. As the bulk of these tissue structures are polarization-sensitive, these changes present an opportunity for a polarization-based monitoring technique during scar formation and healing process, or, for example, during treatment of scars.

Clinical Application

One highly significant application for the present imaging method and its ability to image the peritoneum and the broad ligaments is for patients with endometriosis. While endometrial lesions can be found on many different tissues, these tissues are common locations where endometrial lesions are found.

A brief discussion of the use of the present imaging system and method in the context of an endometriosis procedure will further explain the utility of the present invention. As before, the physician would probably palpate for a fixed, retroverted uterus, adnexal and uterine tenderness, pelvic masses, or nodularity along the uterosacral ligaments. This pelvic examination may reveal uterosacral, cul-de-sac, or septal nodules. Then, laparoscopic examination of the peritoneum would be undertaken. In particular, two to three small incisions are made in the abdomen, the abdomen is distended with carbon dioxide, and the laparoscope and other surgical instruments are inserted into the abdomen at the incision sites. During the procedure, the physician may locate one or more suspected lesions, and then determines their size and developmental stage. Rather than rely upon the prior unassisted visualization techniques, the physician may operably couple imaging apparatus 100 to the laproscope such that the peritoneum field would be illuminated by light source 110 and the remitted light would be directed back along the optical path of the laproscope in association with detection optics 120 toward the plurality of pixels 130. System 100 will process the data and image maps will begin to appear on a video monitor in the surgical suite. The physician can select movie or montage modes for viewing and may be able to manually adjust the parameters of the light, detector and image map valuation to assist in the detection of difficult-to-locate lesions. It is preferred, however, for processing system 200 to be pre-programmed with various protocols for the various types of medical procedure and tissues types that the surgeon may encounter such that the system automatically handles the imaging selection based on the doctor's indication of the type of procedure and tissue being examined.

The present technique and method work well with minimally-invasive surgical equipment. First, this technique allows for image-maps of tissue on the millimeter scale to be constructed. As surgeons scope multiple areas within the peritoneal cavity, a relatively large field-of-view is essential for an efficient and timely procedure. Second, in a laparoscopic procedure, the peritoneal cavity is insufflated as standard protocol so the surgeon has easier access to and visualization of the organs. Insufflation of the abdominal cavity puts a stress upon the peritoneum thus aligning the collagen bundles and causing them to stretch. This will improve the polarization signals remitted from the peritoneum as the orientation of the fibers/bundles will be more linear. With insufflation of the peritoneal cavity during a laparoscopic procedure, the resultant image-maps will provide even higher contrast of the tissue structures than is observed from tissues under slight tension.

Other clinical diagnostics that rely on visual assessment of tissue by the physician could benefit from Stokes-polarimetry imaging. For instance, the present system may be useful in the visualization of nerves in image-guided surgery. In urology, radical prostectomy procedures are performed laparoscopically. The identification of nerves is essential for the surgeon to successfully dissect around them and reducing post-operative complications for the patient involving incontinence and impotence. Better visualization could increase the total nerves spared and give the surgeon greater confidence when working around the nerves.

Another related organ in the urology field where polarization-based imaging may be advantageous is the bladder. The use of ellipticity measurements provided enhanced tissue structural detail about the bladder wall, which may lead to improved detection of abnormal growths, bulges, or tumors within the wall especially when used in conjunction with a cystoscope.

The present system and method may also have utility in improving the diagnosis of various dermatological conditions. For example, the collagen architecture is one factor that indicates a biological difference between benign and malignant melanocytic skin lesions. The collagenous differences may affect the polarization-state of remitted light, and hence the degree of polarization image-maps could possibly indicate locations of tumor center and tumor periphery thereby aiding physician in visualizing excision margins. Because melanocytes are located at the lower part of the epidermis, the appropriate wavelength should be selected for this depth as well as for the chromophores within the various types of nevi.

In another example, normal appearing abdominal peritoneum has its degree of polarization vary predictably. Thus, viewing the image-maps as a function of IPA sequentially (i.e. a short movie) shows that the regions with fine structural detail sweep across the image-map. In FIG. 3, this highly detailed region cycled from the top to the bottom of the image-maps. It is believed that lesions within the abdominal peritoneum disrupt the regular structure of collagen bundles; so, as the IPA is varied, the site(s) where lesions are located will show a discontinuity in the degree of polarization image-maps. A lesion may appear with a degree of polarization dissimilar to the surrounding peritoneum at all, some, or none of the IPAs. The viewing of the image-maps sequentially provides an added dimension; the use of multiple IPAs can be used to aid in differentiating between normal and pathological regions that may be difficult to see from an image-map created with a single IPA.

A non-exhaustive list of imaging modalities that may benefit from the use of system 100 include endoscopy, dermascopy, laparoscopy, colposcopy, and cystoscopy. Stokes-polarimetry imaging could also be used alongside the standard imaging modality to provide further detail about tissue structures not seen with unpolarized light.

We have studied the foregoing in the laboratory and present some examples below to help further elucidate the parameters of the present invention. It should be understood that the parameters, methods and equipment used do not necessarily provide the best mode of using the present invention.

EXAMPLE 1

With cutaneous scars the use of the present imaging system and method results in a relationship between the incident polarization angle (IPA) and the anatomical features of human skin. In short, if the IPA is parallel to the skin tension lines, then greatest contrast can be observed between scar tissue and normal tissue. These results are related to other skin diagnostics; i.e. melanoma and mapping of skin tension lines pre-op for minimal scarring. The results also relate to endometriosis because endometrial lesions contain variable degrees of fibrosis and scar tissue.

Cutaneous scars can be differentiated from surrounding normal skin using Stokes-polarimetry imaging. The use of multiple IPAs elicited image-maps displaying both the scar and surrounding skin with variable DoLP. In general, there was an optimal IPA such that scar tissue could be identified and distinguished from normal skin with greatest contrast. At the optimal IPA, scar tissue remitted light with low DoLP while normal skin retained a greater degree of linear polarization. The optimal IPA correlated with the contours of the relaxed skin tension lines (RSTL) at the location of the scar. In general, when the IPA was parallel to the RSTL (within ±10°) or tangent to a curved RSTL (within ±10°) at the location of the scar, the image-maps showed the greatest contrast between scar tissue and normal skin. The margins and location of the scar tissue were better delineated in image-maps formed with the optimal IPA than with other IPAs.

In general, there was another IPA, approximately 90° away from the optimal IPA, that showed sufficient contrast between scar tissue and surrounding tissue. However, this contrast was never as great as when the IPA was parallel to the skin tension line. We will refer to IPAs that cause this result as the secondary IPA.

Figure 7:
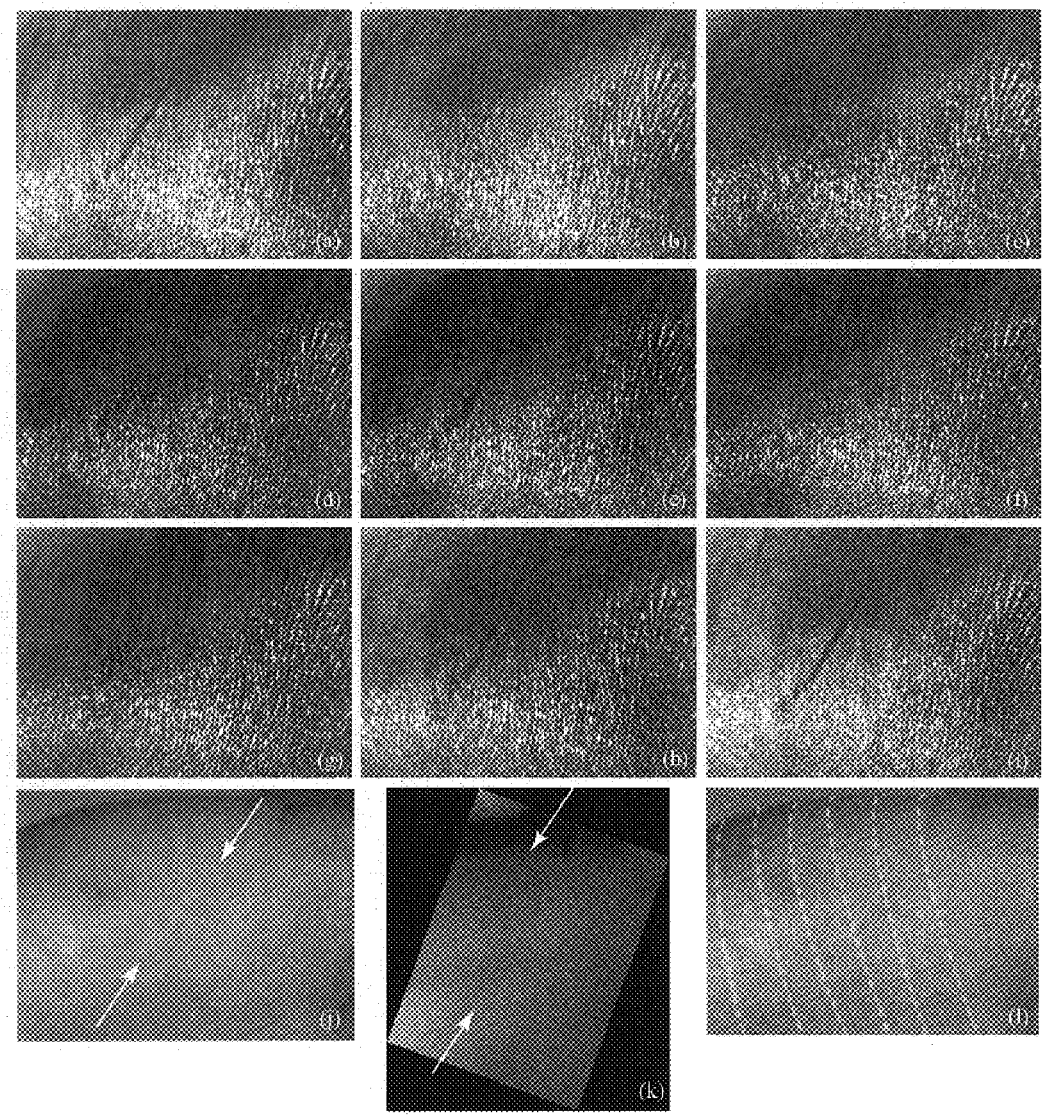
FIG. 7 is a montage of a plurality of image-maps taken of a scar located between the volar and dorsal surfaces of a human hand.

FIG. 7(a-i) displays image-maps taken of a scar located between the volar and dorsal surfaces of a subject's hand. The optimal IPA was approximately 160°, see FIG. 7(i), and the secondary IPA was 80°, FIG. 7(e). FIG. 7(j) and FIG. 7(k) are images of the skin and scar using unpolarized white light and 940-nm light, respectively. FIG. 7(l) displays the skin tension lines overlayed on the color image; the tangents to the skin tension lines are at approximately 160°-170°.

Figure 8:
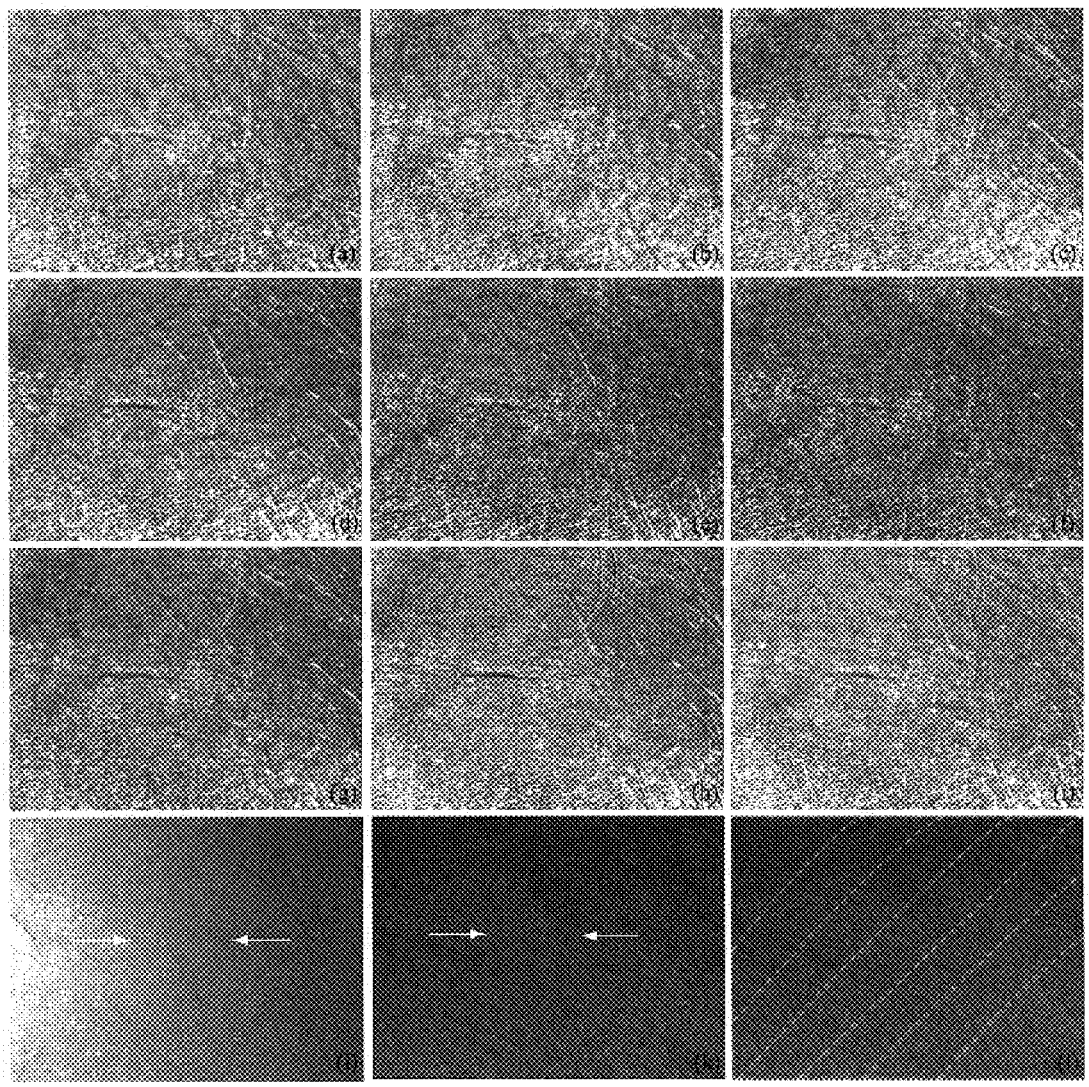
FIG. 8 are DoLP image-maps of the posterior surface of a subject's forearm. The skin region was illuminated with linearly polarized 940-nm light. The IPA was varied in steps of 20°; from 0°(a) to 160°(i). (j) shows a color image formed with unpolarized white light. (k) shows an image formed with unpolarized 940-nm light. (l) shows the skin tension lines (yellow dotted lines) overlayed on top of the color image.

FIG. 8 (a-i) displays image-maps taken of a scar located on the posterior of a subject's forearm. The recently tanned skin resulted in difficult observation of the scar with the naked eye or color photography (FIG. 8(j)), as the scar was slightly camouflaged with the surrounding skin. FIG. 8(k) shows the tissue region illuminated with unpolarized 940-nm light; the scar is not clearly visible. The optimal IPA was in between 40° and 60° (FIGS. 8(c) and (d)), and the secondary IPA was between 120° and 140° (FIGS. 8(g) and (h). The skin tension lines, displayed in FIG. 8(l) are situated at approximately 45°-50°.

Figure 9:
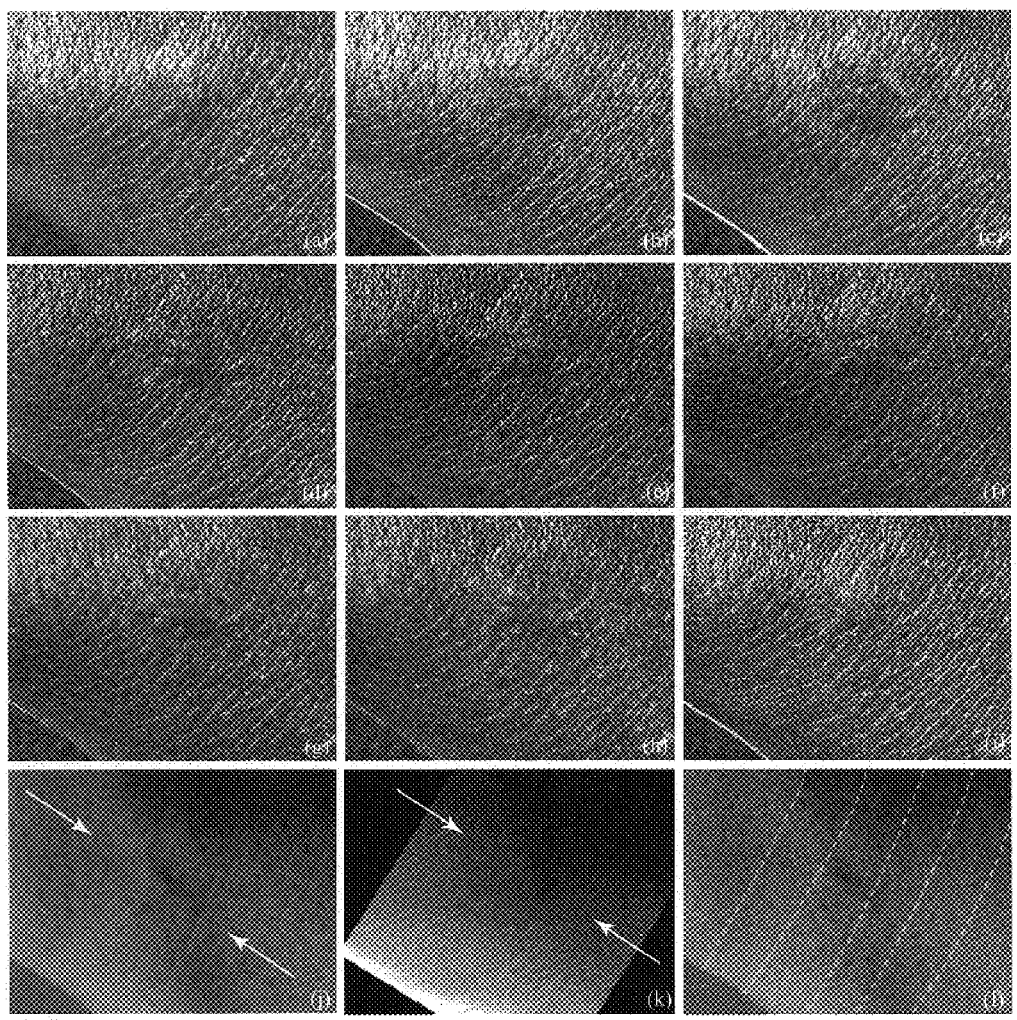
FIG. 9 are DoLP image-maps of the posterior surface of a subject's wrist. The skin region was illuminated with linearly polarized 940-nm light. The IPA was varied in steps of 20°; from 0°(a) to 160°(i). (j) shows a color image formed with unpolarized white light. (k) shows an image formed with unpolarized 940-nm light. (l) shows the skin tension lines (yellow dotted lines) overlayed on top of the color image.

FIG. 9(a-i) displays image-maps taken of a scar located on the posterior surface of a subject's wrist. This scar represents an interesting case because while the color image (FIG. 9(j)) shows the superficial appearance of a narrow scar, the DoLP image-maps shows that the margins of actual scar tissue cover a much larger area. Hence, the scar tissue margins are better delineated in the DoLP image-map while the color image does not provide any indications of this more extensive tissue structural difference. FIG. 9(k) shows the tissue region illuminated with unpolarized 940-nm light; the scar is not clearly visible. The optimal IPA was between 20° (FIG. 9(b)) and 40° (FIG. 9(c)), and the secondary IPA was approximately 100° (FIG. 9(f)). The skin tension lines, displayed in FIG. 3(l), are situated at approximately 30°.

Figure 10:
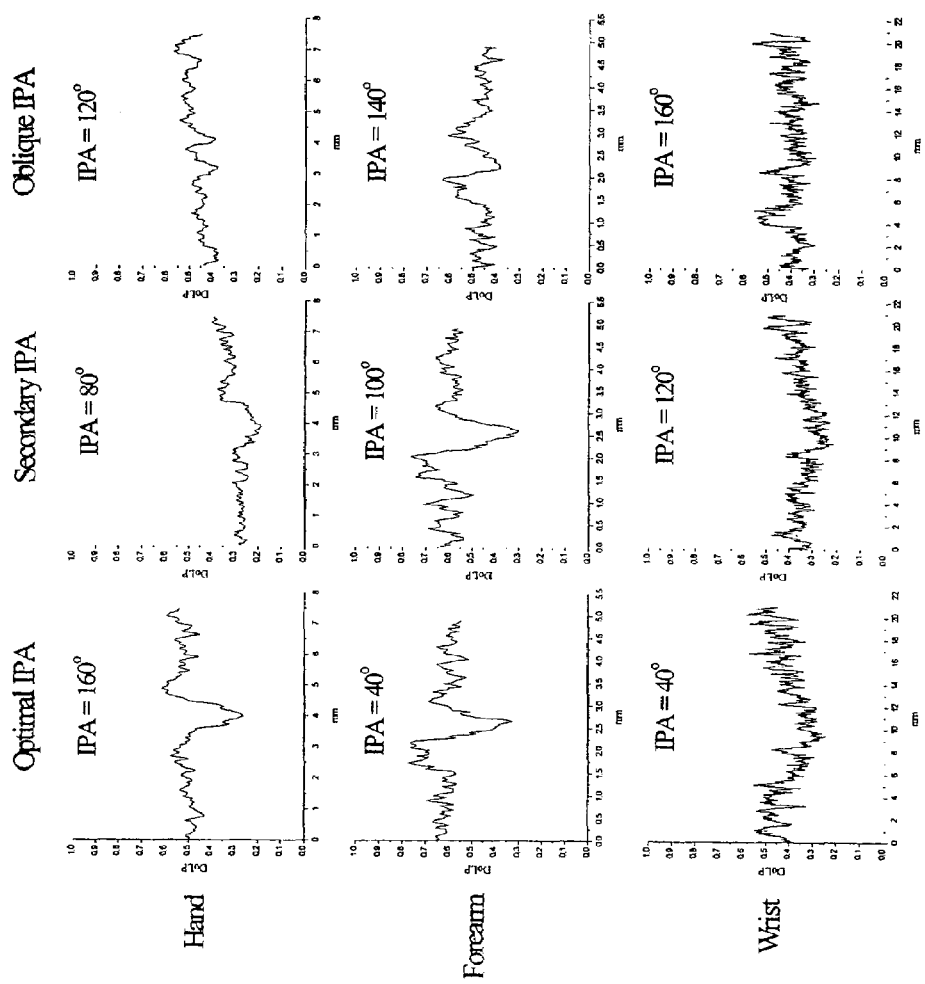
FIG. 10 are plots of DoLP profiles across the scar of Example 1 for the optimal IPA, secondary IPA and an oblique IPA.

FIG. 10 shows plots of the DoLP profiles across the scars for the optimal IPA, secondary IPA, and an oblique IPA. These plot profiles confirm that the contrast between scar tissue and normal tissue follow the relationship: image-map (optimal IPA)>image-map(secondary IPA)>image-map(oblique IPA).

Tension in all directions is usually exhibited across the skin, but there is always one direction where tension is greatest at each region of the body. This direction of maximal tension is indicated by skin tension lines also referred to as cleavage lines, relaxed skin tension lines, lines of elective incision, or Langer's lines. Relaxed skin tension lines are found by pinching or compressing the skin, at the location of interest, in different directions until furrows and ridges appear straightest with the greatest number and extend for a greater distance. Pinching done obliquely will result in an S-shaped pattern while pinching in the incorrect direction causes distorted crumpling. RSTL appear the same in all people.

It is important to note that interpreting the results based solely on the absolute value of DoLP is not what permits image contrast between scar tissue from normal tissue; rather, it is the relative difference between the DoLP values from scar tissue and DoLP values from normal tissue at a specific IPA. It is not until IPA is parallel to the skin tension lines where depolarization due to scattering in the normal tissue is less significant than that of scar tissue; that is, where remitted DoLP from each tissue type is different.

Because the exterior of the human body contains curved surfaces, the skin tension lines also have curvature and may not be perfectly straight at the region of interest. In addition, the resultant image-maps only represent data in two-dimensions. So, depending upon body anatomy, the skin tension lines may not follow straight lines in an image-map. Hence, the curvature of skin tension lines in relation to the IPA may be a factor in causing non-uniform contrast over the imaged area. Locations in the optimal image-map, where IPA was oblique to the skin tension lines by at least 5°, introduced greater birefringence effects into the light, thus causing an altered polarization state relative to surrounding areas. If scar tissue happened to be at these locations, its contrast from normal skin would be less than maximum. For image-maps including areas where skin tension lines have acute curvature, the optimal contrast may only be attributable to a small region. To obtain the most information multiple IPAs may be needed to cover a range of angles pertaining to the tangents of the curved skin tension lines.

As shown in FIGS. 7(a-i), 8(a-i), and 9(a-i), DoLP image-maps formed with the optimal IPA provided an enhanced view that provided easy identification of scar tissue locations. While unpolarized images depend upon scattering and absorption coefficients to influence the intensity of remitted light, DoLP relied on polarization-properties of light.

The literature indicates that even after a laparoscopic examination, it was likely that lesions remain undetected and are left intact to cause further pain and infertility. Current laparoscopy relies on judging the color and texture of these lesions when making diagnoses. The application of Stokes-polarimetry imaging to detection of endometriosis presents a great opportunity to enhance visibility of the lesions and/or their fibrotic components. The data from the above described example show how cutaneous scar tissue was successfully differentiated from normal skin using Stokes-polarimetry imaging; such results can be expected in the identification of endometrial lesions with the presently disclosed imaging technique.

EXAMPLE 2

Although tissues/organs such as the gall bladder, bladder, uterus, and small intestine that exist in the internal abdominal cavity are comprised primarily of smooth muscle walls, experimentation with the present system and method have show that they each have polarization-sensitive constituents that cause uniquely polarized light to be remitted. Additionally, experiments with tissue from a small intestine shows that the SPI image-maps generated by the present system and method reveal the nerves that run around the intestinal wall indicating the feasibility of imaging nerves on prostates and other organs and tissues.

The image-maps from this tissue group indicated that polarization-based imaging of relaxed smooth muscle tissue, in general, lead to little smooth muscle structural information at the millimeter scale compared to image-maps of the abdominal wall peritoneum. The smooth-muscle based image-maps do present indications of relative differences between various tissues-types, and show sensitivity to the different IPAs. As IPA was varied, the remitted polarization state from the smooth muscle tissue did not remain constant.

The distended bladder is unique among this group of tissues in that the muscular wall was stretched thin. This resulted in the packing space between the smooth muscle bundles to be greater than that of undistended smooth muscle-based tissues thus allowing polarized light to interact with the tissue structures without being significantly depolarized by the bulk of denser smooth muscle arrangement. Hence, the image-maps of the distended bladder did show significant tissue structure within the wall.

To understand the minor differences between the various tissues and to relate the polarization-based image-maps to the underlying tissue structure, a review of their structural organization will be discussed. In general, the overall thickness of the muscle wall influenced the remitted polarization state of light. Thick-walled tissues (i.e. relaxed bladder, uterus) caused greater depolarization of the incident light than thin-walled tissues (i.e. small intestine, gall bladder, distended bladder). In thin-walled tissues, there was less material and scatterers to cause complete depolarization of the polarized light. When incident linear polarization was used, the DoLP values of the smooth muscle wall modulated minutely as IPA was changed; the DoCP values modulated more significantly as IPA was changed, see the intestine and gall bladder image-maps. Although this imaging technique, currently limited to one wavelength, cannot indicate which specific layers of the tissue affect the polarization properties of the remitted light, it does indicate how the tissue as a whole affects the properties of the remitted light.

Small Intestine

The wall of the small intestine consists of several layers: mucosa, submucosa, muscalaris propria, and adventitia. Between the longitudinal and circular muscle layers of the small intestine in the muscalaris propia lies the myenteric plexus. The myenteric plexus forms a continuous network around the circumference of the tubular digestive tract. The ganglia, nerve fibers, and nerve bundles form complex networks that innervate the muscle cells. From the degree of circular polarization image-maps, the larger ganglia, especially the ones that compose the primary plexus of the myeneteric plexus, remitted significantly different polarization states than the surrounding tissue. As noted in the literature, the neurons in the primary plexus gather in very large groups, some containing well over 100 neurons. To visualize ganglia of the secondary or teriary plexus would require a CCD camera or similar imaging device with greater sensitivity and higher magnification. Since the neurons of the secondary and tertiary plexus are arranged in a less regular pattern than the neurons of the primary plexus, the use of multiple IPAs would be advantageous. The ganglia are distorted by the movements of the external muscle and overall positioning of the small intestine. So, comparison of features such as the number of ganglia and their thickness must take into account their deformability.

Figure 11:
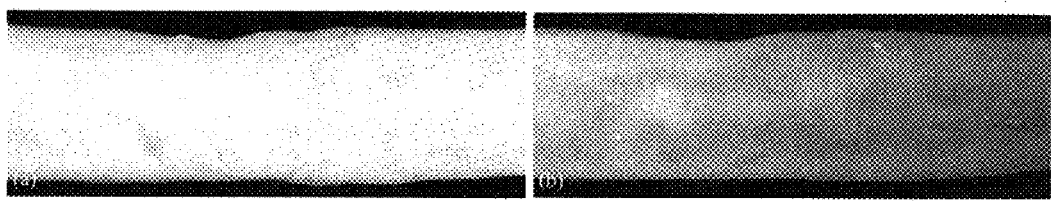
FIG. 11 shows images of the small intestine illuminated with white light and infrared radiation.

FIG. 11 shows images of the small intestine illuminated with white light (a) or 940-nm radiation (b). Note that the light colored vertical lines (corresponding the primary myenteric plexus) is hardly visible.

Figure 12:
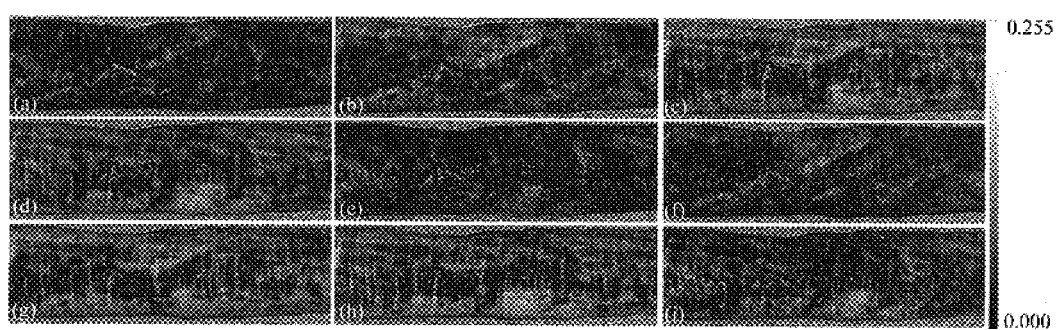
FIG. 12 shows a DoCP image map of the small intestine of FIG. 11.

The DoLP image-maps created with incident linear polarization (not shown) provided slight indications that there were additional structures besides the bulk intestinal smooth muscle wall. At some IPAs, very fine dark lines ran across the width of the intestine. These dark lines show that the incident polarization was depolarized and was remitted with a low degree of linear polarization. In fact, further information about these lines and tissue structure could be gained by looking at the DoCP image-maps that were created with incident linear polarization, as seen in FIG. 12. In the DoCP image-maps, at some IPAs, the lines appeared brighter than the surrounding tissue. This indicates that light was remitted with a higher DoCP than the surrounding intestinal wall. The ganglia converted incident linear polarized light into a more circular form while the surrounding intestinal wall did not, thereby providing contrast between the two tissue types. Similar results were achieved when using incident circular polarized light. As there were indications, from the bright lines across the intestine, that the incident circular polarized light was converted to a more linear form by the ganglia, the DoCP image-maps created with incident circularly polarized light corroborate the fact that light became less circular in nature after interacting with the ganglia. The DoCP image-maps showed dark lines across the intestine indicating that ganglia caused the light to be remitted with very little circular polarization. More importantly, the surrounding smooth muscle retained a higher degree of polarization. These differences in IPA tissue sensitivity provided contrast such that nerve ganglia and muscle tissue, each with unique depolarizing properties, could be distinguished.

Under observation with the present system and method, nerves are polarization-altering tissue that causes incident linear polarization to be converted into a more circular form. The present system can identify these nerve structures.

Bladder

The thickness of a bladder wall depends on the degree of bladder distention—while it is empty, the wall is thickest. When the bladder is fully relaxed, the smooth muscle is closely packed within the tissue. However, when the bladder is distended, the smooth muscle bundles are stretched, and the extra spaces or voids filled with other stretched connective tissue between the smooth muscle fascicles.

Figure 13:
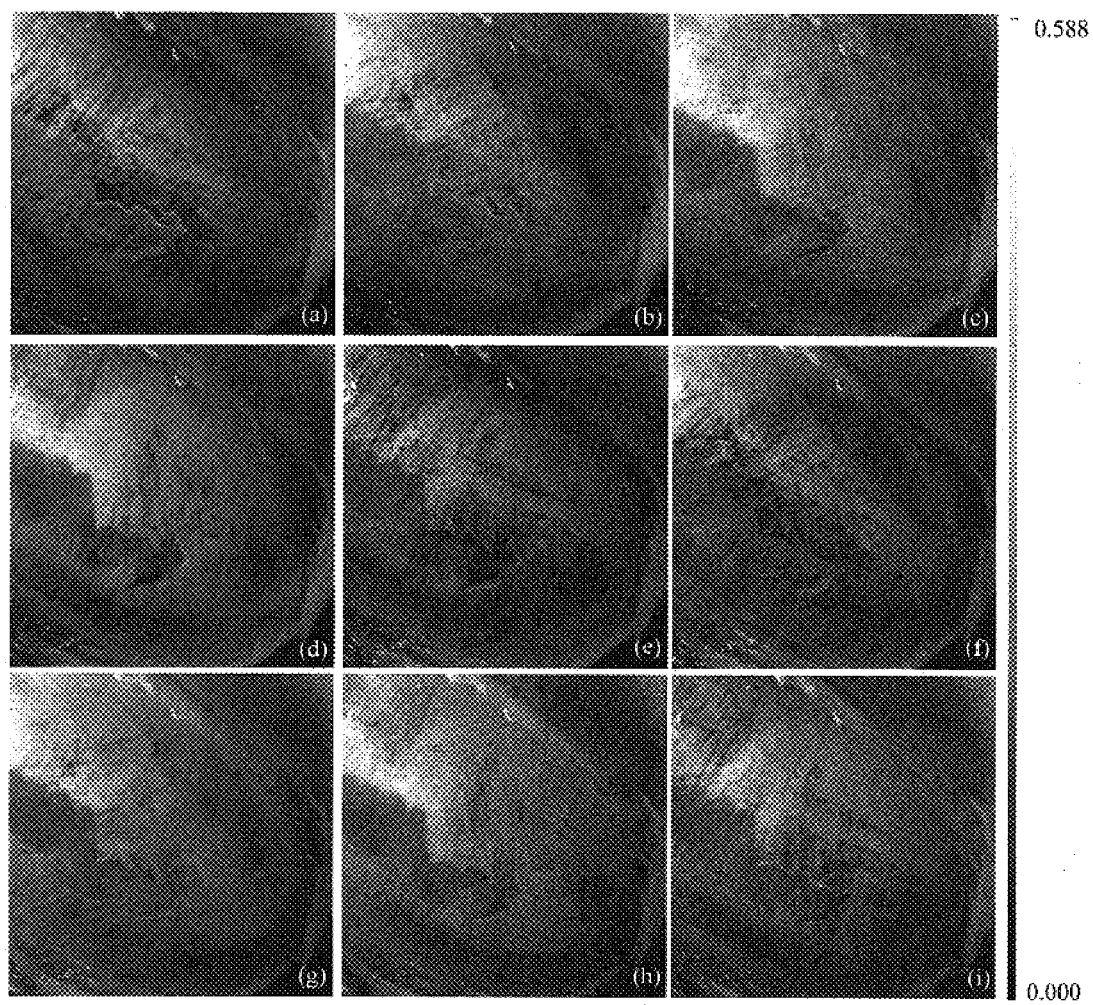
FIG. 13 shows a DoLP image map of a bladder of Example 2.
Figure 14:
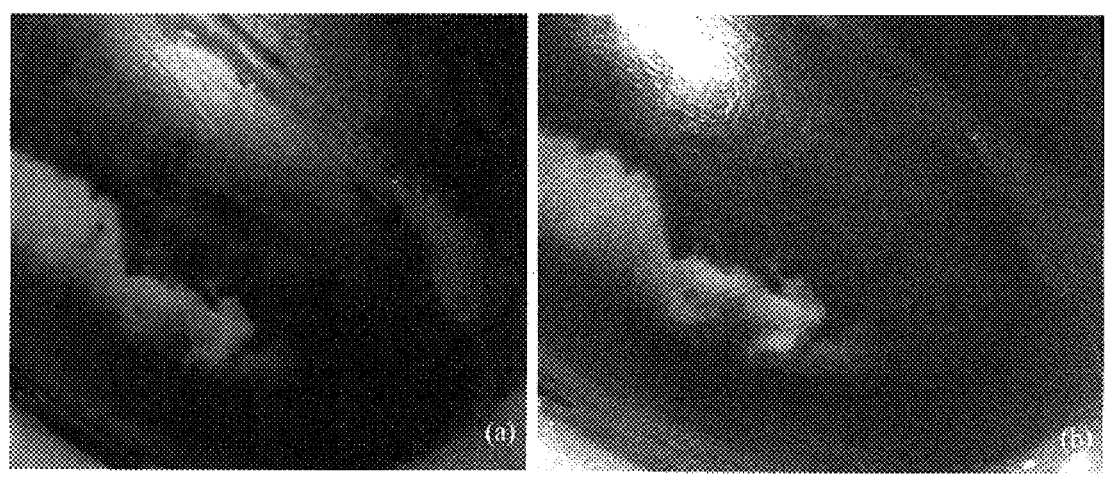
FIG. 14 shows an unpolarized image of the bladder from Example 2.

Light remitted from the distended wall did carry polarization information based upon the tissue structures. The DoLP (FIG. 13) and DoCP image-maps, from both incident linear and circular polarizations, indicated some of the larger aggregated bundles of smooth muscle as seen by the fibrous textures. These image-maps provided much greater information about the tissue structure than either color or near-infrared unpolarized images. As IPA was changed, the textures of the bladder wall changed—since the smooth muscle bundles were situated in various directions on different layers, the interaction of linearly polarized light with the muscle bundles and connective tissue responded differently to different IPAs. These structures were not observable in the unpolarized images of the bladder, FIG. 14.

EXAMPLE 3

Fresh ovine broad ligament and abdominal peritoneal wall were obtained and kept moist with saline-soaked paper towels and refrigerated for less than <3 hours until placed on the imaging system stage. Before imaging the broad ligament and peritoneal wall, these tissues were suspended under slight tension approximately 1 inch above the stage while being held at the corners by hemostatic forceps attached to the imaging stage. The applied tension prevented the tissue from fully retracting. The surface of the stage was covered with a light absorbing material so as to minimize reflection and scattering effects from the stage.

Color photos of the tissue were taken with a digital SLR camera (Canon; D60; Japan) while being illuminated with unpolarized white light from a Xenon light source. Near-infrared images were taken with the visible-NIR sensitive CCD (Hitachi; Japan; KP-F120CL) while the tissue was illuminated with unpolarized 940 nm light from the fiber-coupled laser.

Figure 15:
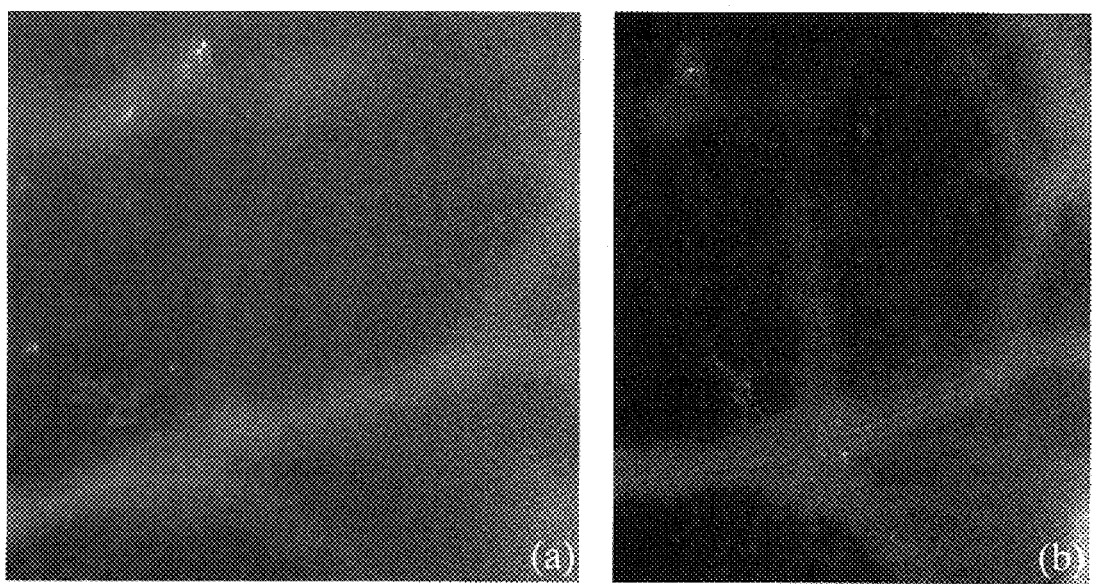
FIG. 15 shows an unpolarized image of the abdominal peritoneum of Example 3.

The images taken with unpolarized 940 nm light, see FIG. 15 (Chapter 8), show very little structure within the tissue. With white light illumination, the peritoneum appears white in color with nearly uniform intensity whereas with near-infrared illumination, the peritoneum also shows little structure except for some of the more prominent vessels and larger collagen bundles.

Figure 16:
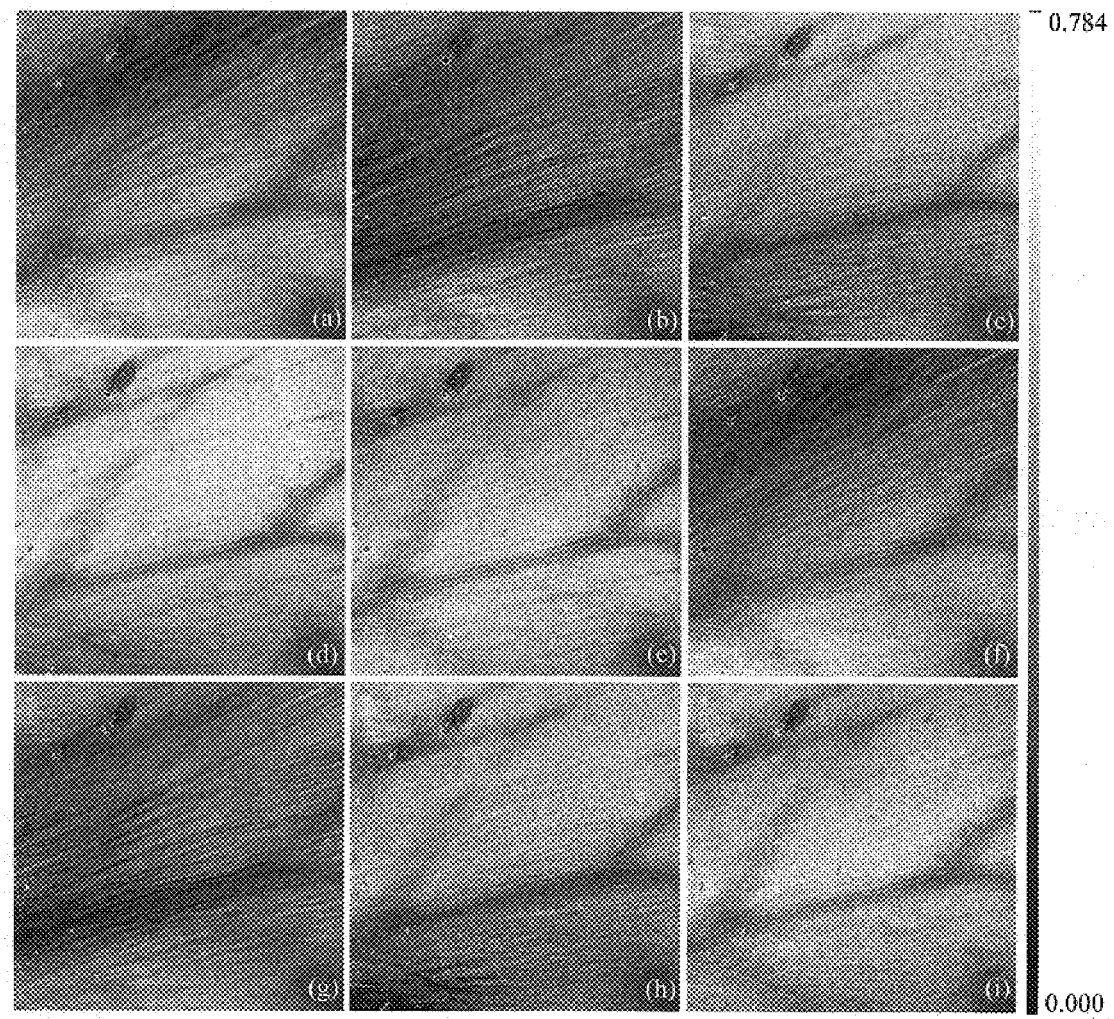
FIG. 16 shows DoLP image-maps of the abdominal peritoneum at various IPAs.
Figure 17:
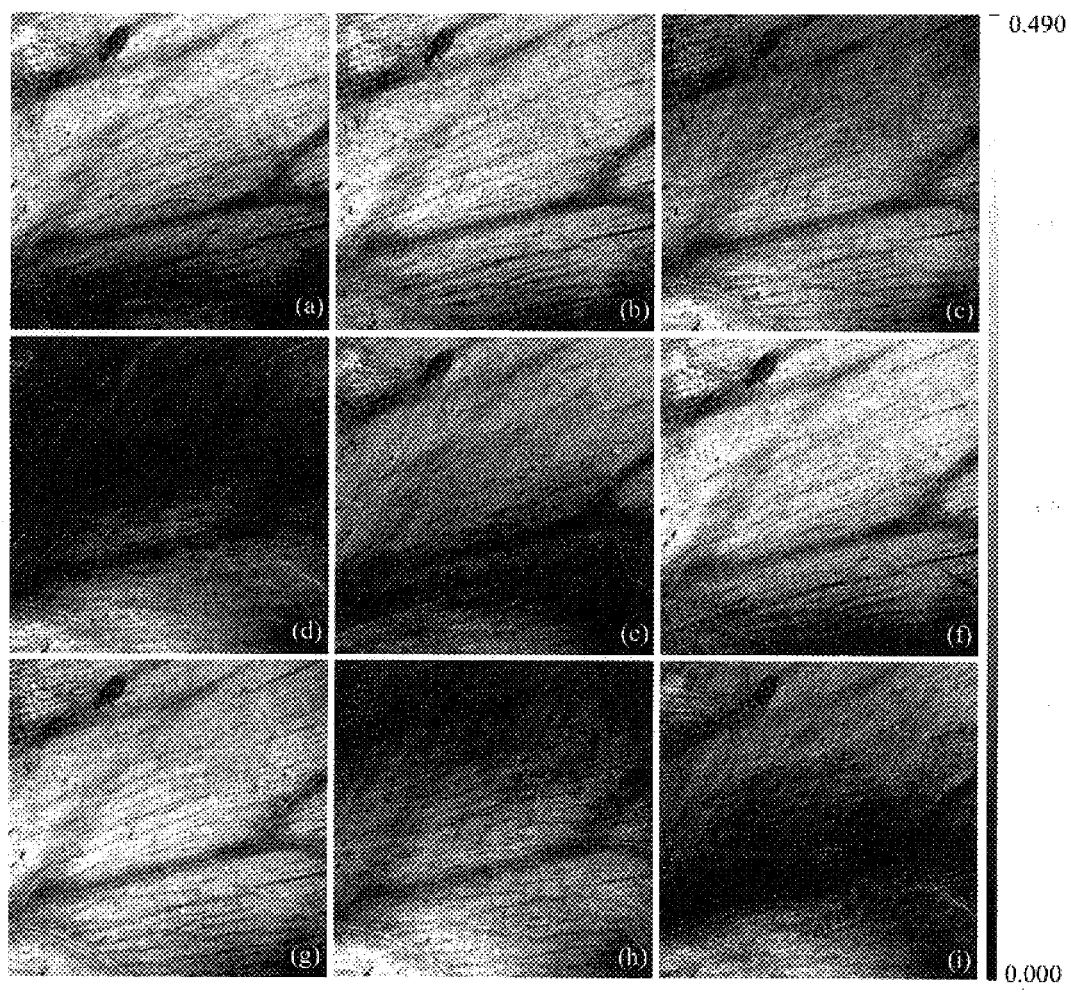
FIG. 17 shows a DoCP image map of abdominal peritoneum with linearly polarized light.

At certain IPAs, such as in FIG. 16(a), (c), (d), (e), (h), (i), the image-maps show the fine structure of the peritoneum. Further, the use of certain IPAs accentuated the appearance of fibrous structures within a certain region of the imaged peritoneum because the fibrous strands ran at different angles with respect to the horizontal. For example, in FIG. 16(a) bundles are highlighted at the top of the image-map and at FIG. 16(h), bundles are highlighted at the bottom of the image-map. At other IPAs, such as in FIGS. 16(d) and (i), the image-maps show a more homogenous appearing peritoneum with relatively high DoLP. The structure shows fibrous strands running laterally to each other and following a general direction. In FIGS. 16 and 17, the directionality of the collagen bundles point from the lower left to the upper right corners of the image-maps at the top of the image-maps but run more horizontally at the bottom of the image-maps. Blood vessels are also visible in the image-maps and appear darker than the surrounding peritoneum. The blood vessels are visible in the image-maps (e.g. FIG. 16(b)) except where the signal from the overlying peritoneum masked the signal from the deeper blood vessel (e.g. FIG. 16(d)).

In FIG. 15, 16, 17, 18, there are two pieces of fat located in the upper left corners of the image-maps. The DoLP values for these areas did not change over the range of IPAs and always remitted low DoLP, see FIG. 16(d).

The DoCP image-maps created with linearly polarized light, FIG. 17, also show the fibrous structure of the peritoneum. The appearances of the bundles are slightly different compared to their appearances in the DoLP image-maps. Here, although some of the bundles are observed, they do not appear as distinct as they do in the DoLP image-maps. The image-maps indicate that the collagen bundles generally point in the same direction as they do in the DoLP image-maps—e.g. towards the lower left or upper right corners along the top of FIG. 16. The DoCP image-maps also indicate that other components of the interstitial matrix may be affecting the circular polarization of remitted light causing the bundle pattern to seem less regular.

At certain IPAs, there are sections of the image-maps that appear mostly dark. From looking at the series of DoCP image-maps, the position of this dark area moves systematically in the image-maps: for example, in FIG. 17 from the low part of the image (a), to the middle (b) and then to the top (c).

Figure 18:
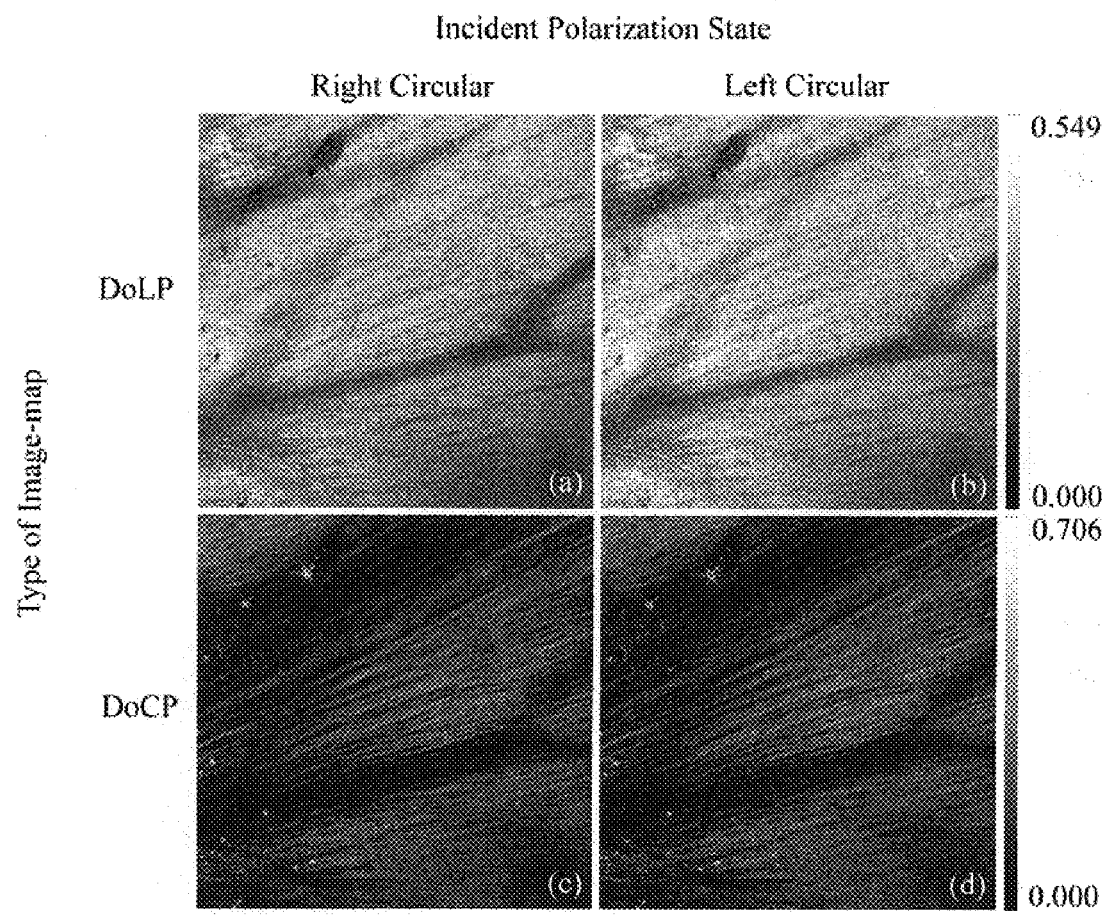
FIG. 18 shows a DoLP image map of abdominal peritoneum with circularly polarized light.

The DoLP image-maps, FIGS. 18(a) and (b), show less defined structure within the peritoneum. Though the structure is not as detailed as that which is displayed in other image-maps, i.e. FIG. 17, there is still enough information indicating the direction that the fibers were oriented. In FIG. 18, the blood vessels are visible and the polarization signals from these areas are different than those from the peritoneum.

The DoCP image-maps created with circularly incident light, FIGS. 18(c) and (d), shows structural details. The peritoneum appears with a fine pattern of collagen bundles extending in a striped arrangement with approximately the same directionality as described above. Blood vessels are also observed; however, the polarization signal from the peritoneum sometimes masked the blood vessels. Overall, these DoCP image-maps show more structural information than the DoLP image-maps created with incident circular polarization. Image-maps produced with either left or right incident circular polarization appear very similar with no noticeable differences.

EXAMPLE 4

Immediately following euthanasia, the abdominal peritoneal wall of two cats were surgically exposed for imaging: midline abdominal incisions were made and the peritoneal cavities opened. With two additional oblique incisions, flaps of the peritoneal walls were created so that they folded over exposing the interior of the peritoneal walls. Two corners of each peritoneal wall flap were held by hemostatic forceps and suspended under slight tension approximately 2 inches above the imaging stage. The tissues were kept moist with periodic application of saline solution.

Figure 19:
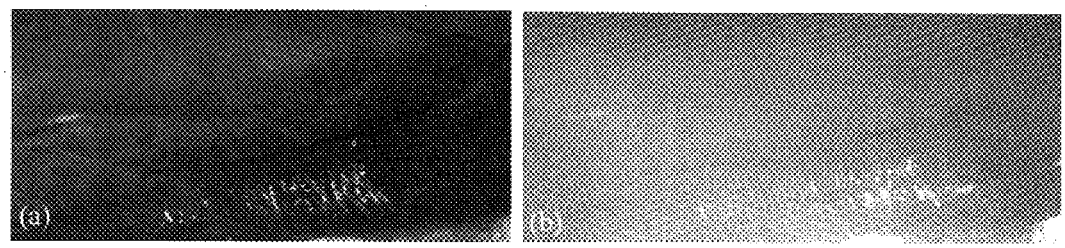
FIG. 19 shows unpolarized images of a feline peritoneum.

To explore the effects from the underlying abdominal wall, the cat peritoneum was imaged while it was still attached to the abdominal wall. Images were acquired of a cat peritoneal wall while being illuminated with unpolarized white light and 940 nm light, see FIG. 19.

Figure 20:
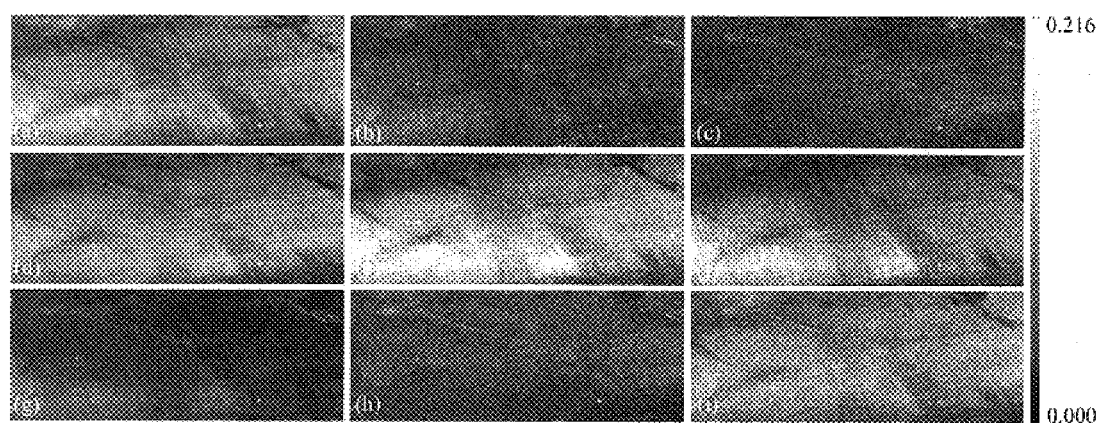
FIG. 20 shows DoLP image-maps of the feline peritoneum of FIG. 19 at various IPAs.

The fine fiber structure of the peritoneum is visible in the DoLP image-maps, see FIG. 20. In the image-maps, the fiber bundles run vertically but slightly angled downwards from left to right. The overall structure does not appear as crisp as it does in the ovine peritoneum image-maps. The fiber bundles appear much thinner and finer than the fiber bundles in the ovine peritoneum; thus individual fiber bundles are difficult to discern from one another. At certain IPAs, as in FIG. 20(a), (e), the fiber structure is more apparent, but at other IPAs, as in FIGS. 20(c) and (h) the tissue appears rather uniform with no structure.

The fibers are also observed in the DoCP image-maps (not shown). At some IPAs, the tissue appears with very low DoCP and no structures are observed. At other IPAs, the fiber-bundle structure appears with a striped pattern alternating between dark and light regions.

The fiber-bundle structure in the DoLP image-maps (not shown), is not observed when incident circular polarization was used. The information gained from these image-maps is about the same as that gained from the unpolarized near-infrared image.

The images formed with incident circular polarization had very low DoCP. These image-maps do not reveal any new information about peritoneal structure. It should be noted that with left-circular polarization, some minimal fiber structure can be seen on the left side of the image-map, however this structure is much less distinct than in the DoCP image-maps formed with incident linear polarization.

It is important to note that the image-maps of cat peritoneum (FIG. 20) differ from those of ovine peritoneum (FIGS. 16-18). Ovine are much larger animals than cats; accordingly, the ovine peritoneum is thicker and consists of larger diameter collagen fiber bundles. In the image-maps, the bundle structures in the cat peritoneum are not as distinct as in the ovine peritoneum image-maps. The widths of the bundle structures are finer and thus are not well represented by the limited resolution of the camera CCD (an area approximately 31×31 μm on the tissue is represented by one pixel). Another difference is that the cat peritoneum was still attached to the muscular abdominal wall during the imaging procedure while the ovine peritoneum was separated from the abdominal wall immediately after post-mortem. By having a muscular abdominal wall beneath the peritoneum, the remitted polarization signals from the muscle tissue influenced the overall detected signal. Furthermore, the near-infrared light penetrated through the peritoneum and scattered within the muscular wall causing some depolarization of light. It may be advantageous to select a wavelength of light, other than that in the near-infrared, that has less penetration depth (e.g. green or blue) to limit the scattered polarized light to be remitted from the peritoneum and not from the underlying muscle. However, for deeper endometrial lesions, the use of near-infrared light should still be considered. Indeed, imaging of the ovine peritoneum, devoid of the muscular wall, shows the polarization properties of light remitted from the tissue of interest without effects from underlying layers.

EXAMPLE 5

Figure 21:
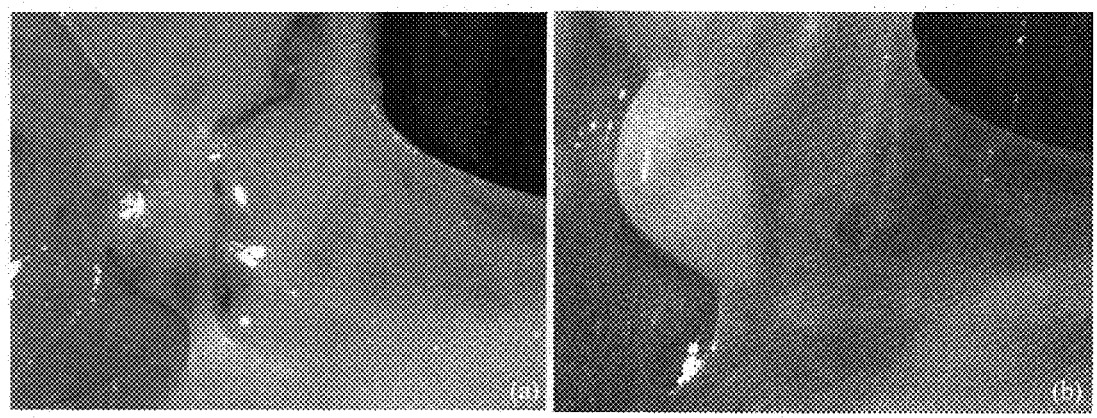
FIG. 21 shows an ovine broad ligament and ovary illuminated with unpolarized light.

FIG. 21 shows an ovine broad ligament and ovary illuminated with unpolarized light. The broad ligament appears rather smooth in texture in these intensity-based images.

In general, the structures observed in the broad ligament polarization-based image-maps are much less ordered than that of the peritoneum. As various regions within the broad ligament have slightly different tissue structures, the figures are representative of most of the observed characteristics, which are best viewed as a consecutive sequence of images, or as a video. The image-maps of the broad ligament also include an ovary which appears here as a region of dark pixels. The degree of polarization scale, for these image-maps, was optimized for the broad ligament and not for the ovary (i.e. the ovary more strongly depolarizes light than the broad ligament). With proper scaling, variations within the ovarian tissue structure can also be visualized.

In the literature, the broad ligament is referred to as a double fold of peritoneum. On the microscopic level, each of these tissues may seem very similar in terms of composition; however, on the millimeter scale, the polarization-based image-maps show that they have somewhat different structural arrangements. The literature usually presents histological views of tissue that are thin cross-sections of the peritoneum. Studies have not taken these cross-sections across the entire peritoneum with the intention of locating and characterizing the larger continuous structures such as the collagen bundles. In addition, the histological processing of the tissue may distort positioning of these constituents.

The remitted light comes from both folds of peritoneum, and the Stokes-polarimetry imaging technique can not differentiate between light remitted from each of the separate folds; hence the image-maps display a mix of signals from both layers of peritoneum. Overall, it is more difficult to judge the directionality of fibers in the broad ligament than in the abdominal peritoneum. In contrast, the polarization signals from the peritoneum are directly from the one fold of peritoneum, hence the image-maps have higher fidelity.

The DoLP image-maps (not shown) of the broad ligament reveal that the fiber bundles in the broad ligament are not unidirectional. There are areas in the broad ligament where a group of fiber-bundles share the same orientation, but a neighboring area may have fiber-bundles pointing in a different direction. There are also areas in the broad ligament where fiber-bundles with different directionality are layered and lie on top of each other. By looking at the set of image-maps, one can visualize the directionality of fiber-bundles at different locations within the broad ligament.

Figure 22:
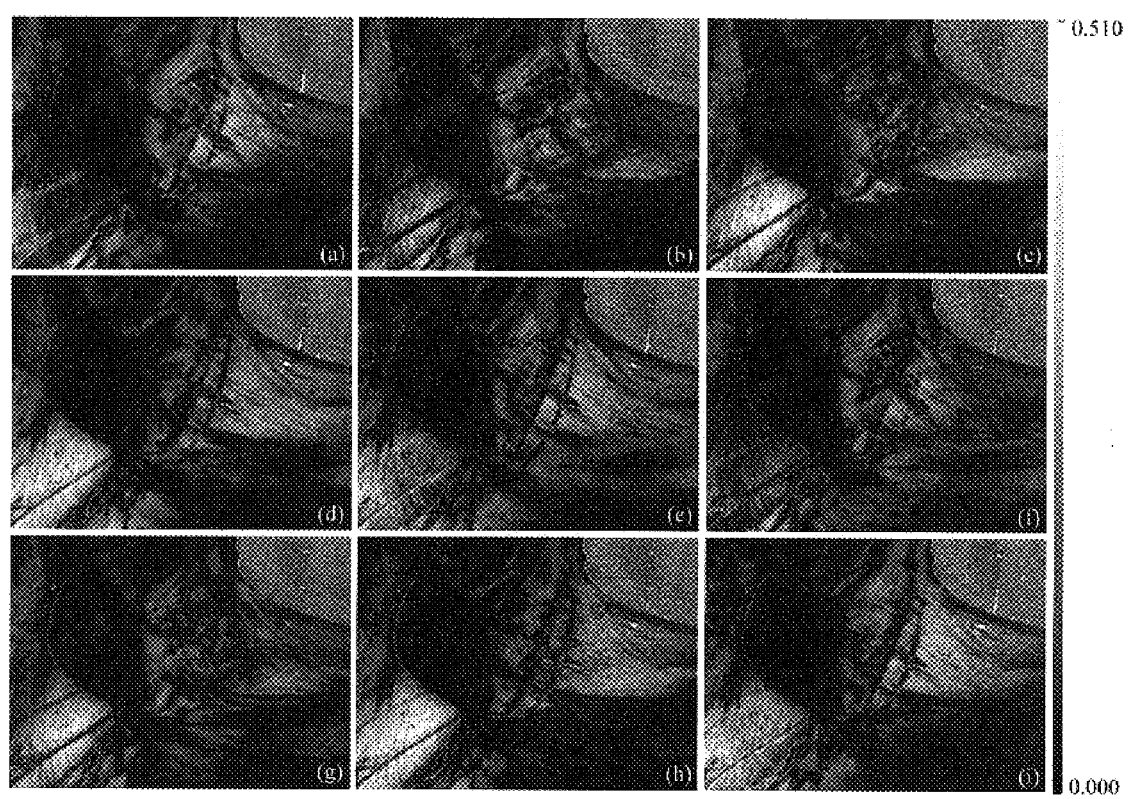
FIG. 22 shows DoCP image-maps of the ovine broad ligament and ovary of FIG. 21.

The DoCP image-maps, FIG. 22 reveal the fiber bundle structures within the broad ligament with greater contrast than the DoLP image-maps do. Within individual image-maps, greater details about fiber-bundle directionality can be observed compared to DoLP image-maps. Although the fiber-bundle directionality across the entire broad ligament is not constant, the DoCP image-maps show the contours of the various structures. When there are overlaying fiber layers with different directionality, these areas can also be visualized.

Some fiber structures can also be observed in the image-maps formed with incident circularly polarized light Although some tissue structure is visible, it is not as extensive as some of the DoLP and DOCP image-maps with incident linear polarization. Variations between the image-maps illuminated with right or left circular polarization were minimal.

The structural details revealed in these image-maps are comparable to those in DoCP images with incident linear polarization. Fiber-bundle structures can be observed pointing in different directions depending on their location in the broad ligament. Variations between the image-maps illuminated with right-circular or left-circular polarization were minimal.

In summary, all degree of polarization image-maps improved the visibility of tissue structures in the broad ligament when compared to the unpolarized white and near-infrared images.

EXAMPLE 6

Although tissues/organs such as the gall bladder, bladder, uterus, and small intestine that exist in the internal abdominal cavity are comprised primarily of smooth muscle walls, experimentation with the present system and method have show that they each have polarization-sensitive constituents that cause uniquely polarized light to be remitted. Fresh ovine tissue (gall bladder and uterus) were obtained and kept moist with saline-soaked paper towels and refrigerated for less than 3 hours until placed directly on the imaging system stage. The surface of the stage was covered with a light absorbing material so as to minimize reflection and scattering effects from the stage.

Gall Bladder

Figure 23:
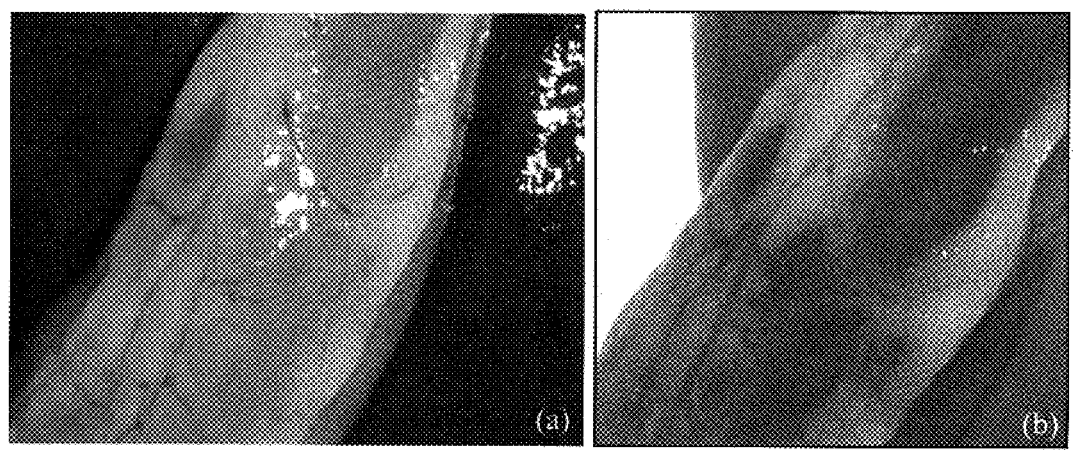
FIG. 23 shows an ovine gallbladder illuminated with unpolarized light.
Figure 24:
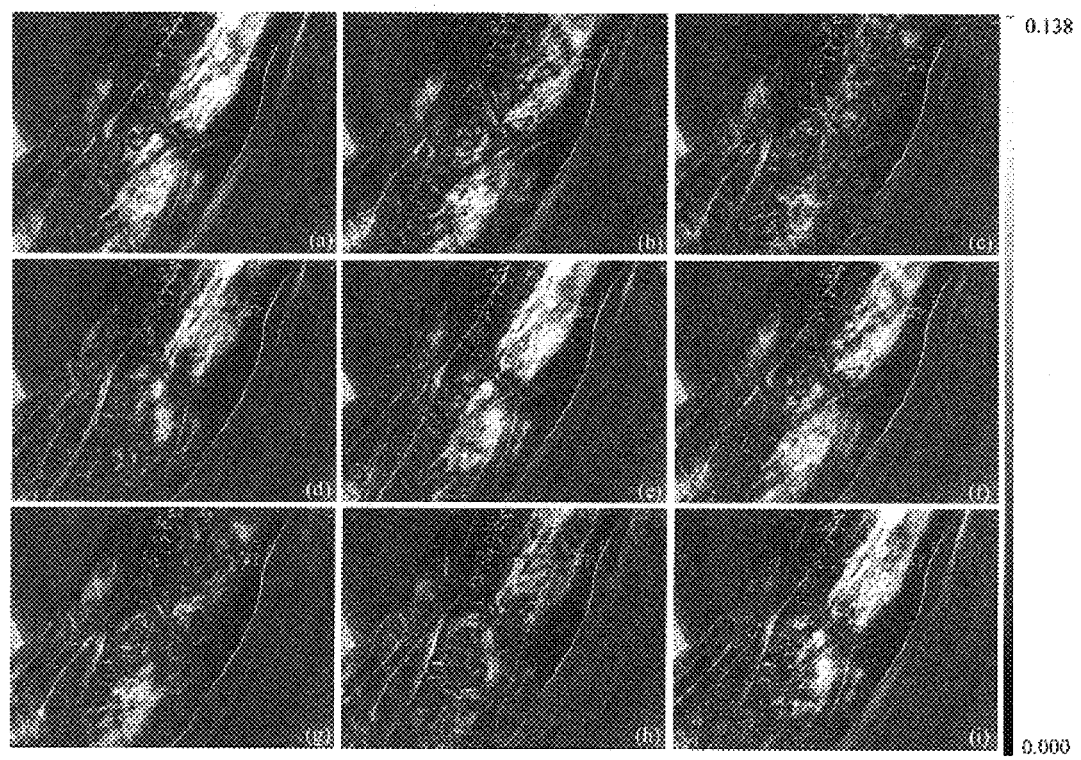
FIG. 24 shows DoCP image-maps of the ovine gallbladder of FIG. 23 as the IA was varied.

An image of the gall bladder formed with unpolarized illumination is displayed in FIG. 23. The image-maps show the exterior of a typical ovine gall bladder. The maps indicate that the gall bladder wall remits higher DoLP than fat. The spots located in the upper region of the image-maps were caused by specular reflection. The DoLP of the spots did not vary according to IPA as it represented locations of glare that reflected into the detector maintaining its original polarization.

Observation of a series of DoCP image-maps with varying IPA appears to provide additional information regarding the tissue smooth muscle wall of the gall bladder (and like organs). The gall bladder wall had significant DoCP modulation as IPA was varied. As seen in FIG. 24(a)-(i), the DoCP from the gall bladder wall was highly dependent on the IPA. The locations where fat was located did not change over the range of IPAs. When IPA=0°, there was much greater DoCP at the gall bladder wall than when IPA=40°. Different structural components of the gall bladder wall were highlighted as IPA was varied. There were certain ranges of IPAs that caused light to be remitted with a very low DoCP suggesting that structures within in the gall bladder wall had different indices of refractions. As such, some pathological changes in the wall may affect the DoCP and/or DoLP values or the modulation pattern of DoCP and/or DoLP values as IPA is varied.

Uterus

Figure 25:
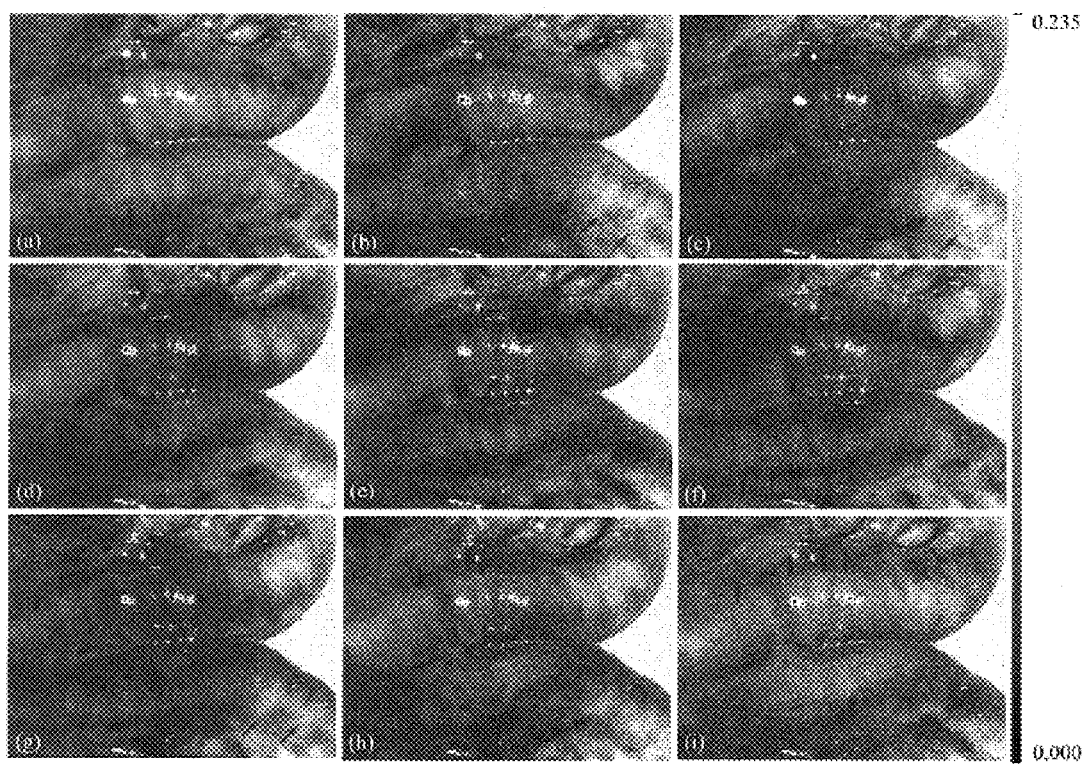
FIG. 25 shows DoLP image-maps of a uterus under polarized light.
Figure 26:
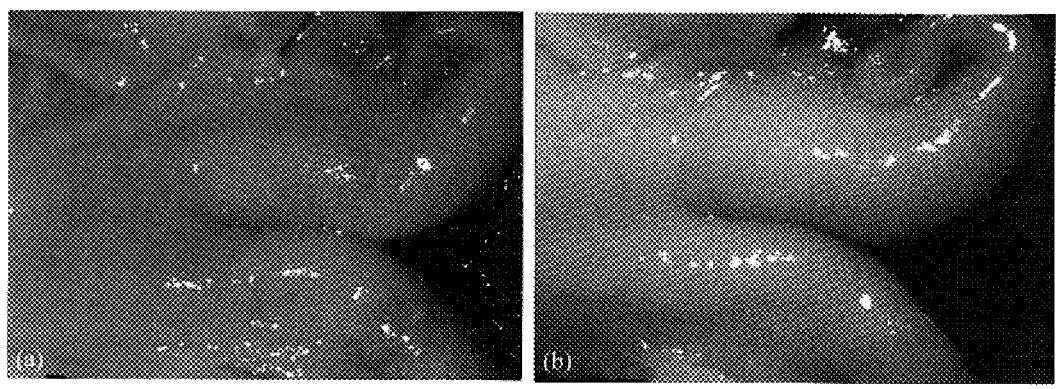
FIG. 26 shows DoLP image-maps of a uterus under unpolarized near infrared light.

The image-maps (FIG. 25) showed a variety of DoLP values such that the uterus did not appear with uniform grey-levels. At different IPAs, the overall appearance of the uterus changed. Of interest is the alternating pattern of light and dark sections that run along the length of the uterine horns (not present in the human uterus), as indicated by the arrows. It should be noted that this pattern is visible in some sections of the unpolarized white light image but not in the unpolarized near-infrared light image, FIG. 26. So, in essence, the DoLP image-maps provided additional information over the intensity-based NIR image. At other IPAs, no additional tissue structures were revealed by the DoLP image-maps, however, slight variations in the uterine wall could be observed.

EXAMPLE 7

Figure 27:
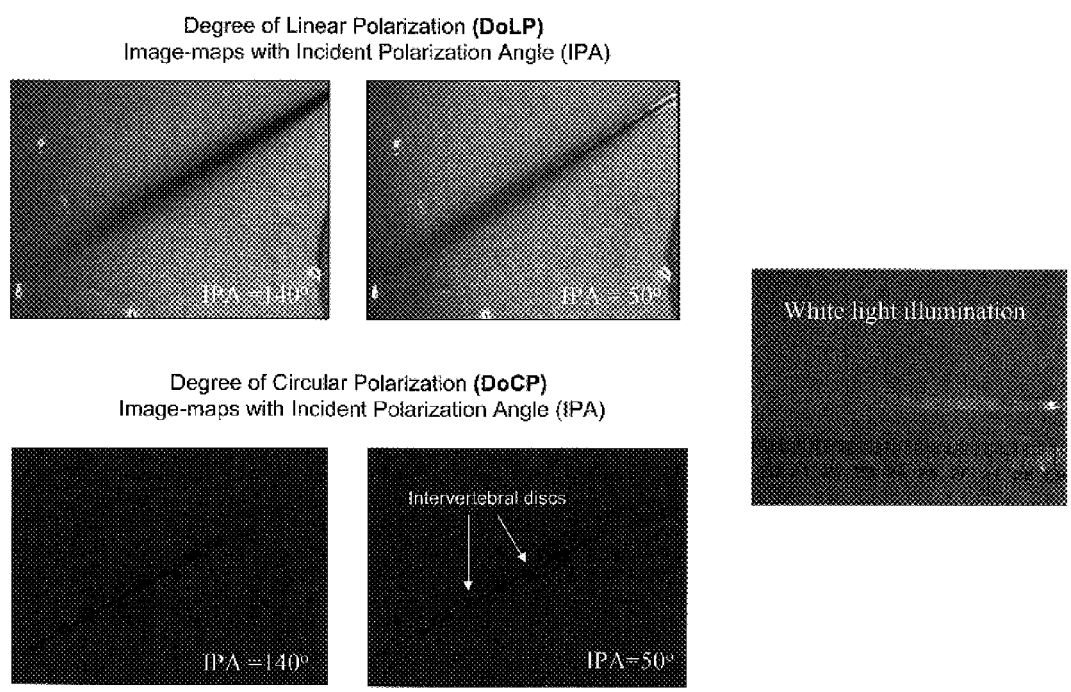
FIG. 27 shows image of a rat-tail under unpolarized light.

This example shows Stokes polarimetry imaging used to differentiate macroscopic tissue structures (rat tail tissue) embedded within a turbid medium. When using unpolarized light, the individual structures in the rat tail cannot be distinguished; only the general shape of the tail can be observed as seen in FIG. 27. However, by using polarized light together with Stokes-polarimetry, the visibility of various known structures such as tendon, soft tissue and intervertebral discs could be improved and contrasted between one another. In particular, the tendons, a birefringent material within a turbid medium, remits different polarizations depending on the IPA. Rat tails of euthanized adult Sprague-Dawley rats (350-400 g) were harvested immediately post-mortem by transection at the proximal end.

The epidermal and dermal layers were dissected away leaving the rat tail tendons, connective tissue, underlying tissue and skeletal structure intact. The rat tail was suspended inside a plastic container with the tail's long axis at a 15° angle with respect to the bench-top surface. A turbid-gel mixture (at 940 nm: $\mu_s'=0.26$ cm$^{-1}$; $\mu_a=0.025$ cm$^{-1}$; transport mean free path (mfp')=3.51 cm) was used to fill the container and hence embed the tail.

FIG. 27 shows a representative DoLP image-map of the rat tail where the incident polarized light (IPA=140°) had undergone strong depolarization during interaction with the rat tail tissue. The shape of the rat tail is shaded by dark pixels, and no information is revealed regarding rat-tail structure besides its basic shape and outline. The dark pixels indicate that the incident polarized light had been significantly depolarized when interacting with the rat tail tissue and that the remitted light retained very little of its initial polarization. This morphology is categorized as "all depolarized", as indicated in Table I.

TABLE I

Morphologies observed in DoLP mappings at various incident polarization angles, rat-tail orientation angles, and rat-tail geometries.

| Incident Polarization Angle | Rat-tail Orientation Angle (f) | | | | | | |
|---|---|---|---|---|---|---|---|
| | Neutral position 0° | 30° | Rat-tail tilted away from the light source 60° | 90° | 120° | 150° | Neutral positon 180° |
| 0° | band-type II | ~band-type II | all depolarized | tendon | all depolarized | ~band-type I | band-type II |
| 10° | band-type II | band-type II | all depolarized | tendon | tendon | all depolarized | band-type II |
| 20° | ~band-type II | band-type II | all depolarized | tendon | tendon | all depolarized | band-type II |
| 30° | all depolarized | band-type II | ~band-type I | all depolarized | tendon | all depolarized | ~band-type II |
| 40° | all depolarized | band-type II | band-type I | all depolarized | tendon | tendon | all depolarized |
| 50° | all depolarized | ~band-type II | band-type I | all depolarized | tendon | tendon | all depolarized |
| 60° | band-type II | all depolarized | band-type I | ~band-type I | all depolarized | tendon | ~band-type II |
| 70° | band-type II | all depolarized | band-type I | band-type I | all depolarized | tendon | band-type II |
| 80° | band-type II | all depolarized | ~band-type I | band-type I | all depolarized | tendon | band-type II |
| 90° | band-type II | tendon | all depolarized | band-type I | ~band-type I | tendon | band-type II |
| 100° | band-type II | tendon | all depolarized | band-type I | band-type I | all depolarized | band-type II |
| 110° | ~band-type II | tendon | all depolarized | band-type I | band-type I | all depolarized | band-type II |
| 120° | all depolarized | tendon | tendon | ~band-type I | band-type I | all depolarized | ~band-type II |
| 130° | all depolarized | tendon | tendon | all depolarized | band-type I | ~band-type I | all depolarized |
| 140° | all depolarized | ~tendon | tendon | all depolarized | ~band-type I | band-type I | all depolarized |
| 150° | ~band-type II | all depolarized | tendon | all depolarized | all depolarized | band-type I | ~band-type II |
| 160° | band-type II | all depolarized | tendon | tendon | all depolarized | band-type I | band-type II |
| 170° | band-type II | all depolarized | tendon | tendon | all depolarized | band-type I | band-type II |

TABLE I-continued

Morphologies observed in DoLP mappings at various incident polarization angles, rat-tail orientation angles, and rat-tail geometries.

| Incident Polarization Angle | Rat-tail Orientation Angle (f) — Rat tail tilted toward the light source | | | | |
|---|---|---|---|---|---|
| | 30° | 60° | 90° | 120° | 150° |
| 0° | mixture | mixture | mixture | mixture | mixture |
| 10° | mixture | all depolarized | mixture | mixture | all depolarized |
| 20° | mixture | all depolarized | mixture | mixture | all depolarized |
| 30° | mixture | mixture | mixture | mixture | mixture |
| 40° | mixture | mixture | all depolarized | mixture | mixture |
| 50° | mixture | mixture | all depolarized | mixture | mixture |
| 60° | mixture | mixture | mixture | mixture | mixture |
| 70° | all depolarized | mixture | mixture | all depolarized | mixture |
| 80° | all depolarized | mixture | mixture | mixture | mixture |
| 90° | mixture | mixture | mixture | mixture | mixture |
| 100° | mixture | all depolarized | mixture | mixture | all depolarized |
| 110° | mixture | all depolarized | mixture | mixture | all depolarized |
| 120° | mixture | mixture | mixture | mixture | mixture |
| 130° | mixture | mixture | all depolarized | mixture | mixture |
| 140° | mixture | mixture | all depolarized | mixture | mixture |
| 150° | mixture | mixture | mixture | mixture | mixture |
| 160° | all depolarized | mixture | mixture | all depolarized | mixture |
| 170° | all depolarized | mixture | mixture | all depolarized | mixture |

Figure 4:
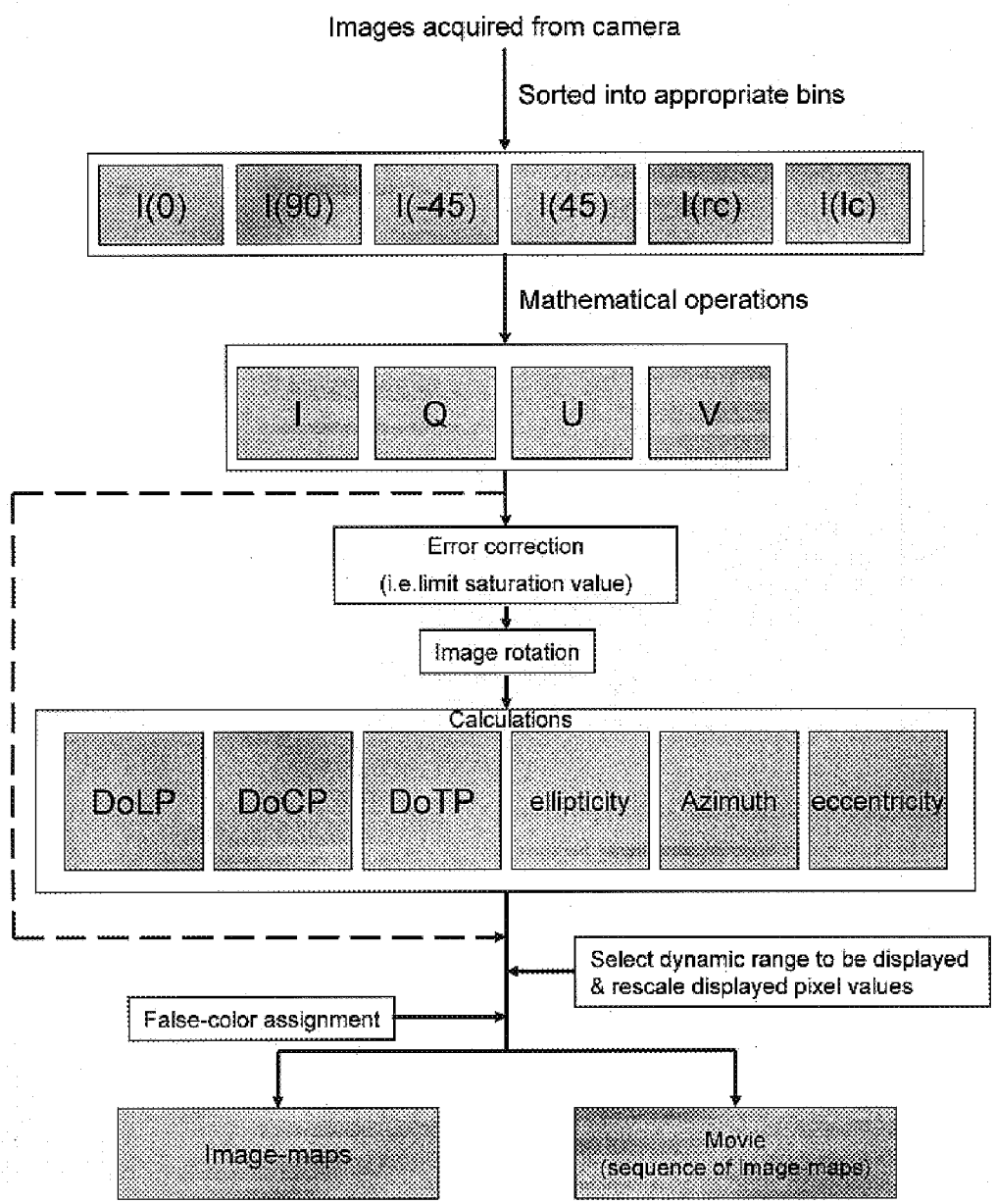
FIG. 4 is a functional flowchart of the imaging system.

Notes:
"band - type I" indicates that there is a regularly occuring banding pattern indicating alternating regions of polarization and depolarization of remitted light along the length of the tail, see FIG. 4(a).
"band - type II" indicates that there is a regularly occuring banding pattern similar to that observed in "band - type I" with the exception of that the depolarization of light at these banded regions was not as distinct, see FIGS. 4(g) and (i).
"tendon" indicates that only the parallel tendons running the length of the rat tail are observed, see FIG. 4(c).
"all depolarized" indicates that the light remitted from all sections of the rat tail is significantly depolarized. Besides the basic shape of the tail, no rat-tail or tissue structures can be discerned, see FIGS. 4(b), (e), and (h).
"mixture" indicates that a morphology that is a combination of the morphologies "band" and "tendon" where the parallel tendons running the length of the rat tail are interspersed by weakly depolarized regions, see FIGS. 4(d) and (f).
~ indicates an intermediate morphology
polarizer angle tolerance = ±1°
rat-tail orientation angle tolerance = ±1°

When light with IPAs of $\phi$ interacted with the rat-tail tissue, one observes not only parallel tendons but also a regular banding pattern along the length of the tail, see FIG. 27. Note that with IPA of $\phi$, the DoLP at the location of the bands is significantly lower compared to the DoLP of the adjacent regions along the tendon, as displayed in FIG. 4(a). Conversely, with IPA of $\phi+90°$, the DoLP measurements do not show significant changes along the length of the tendon.

Not surprisingly, the range of IPAs at which certain morphologies are observed shift according to the orientation angle of the rat tail. For example, the parallel tendons are observed when the IPA was within 90°-140° for $\phi=30°$. But when $\phi=60°$, a shift of 30°, the parallel tendons are observed when the IPA was within 120°-170° (i.e. centered at $\phi+80°$).

The reason for this dependent relationship between observed morphologies and IPA is due to linear birefringence. Rat-tail tendon is made up of collagen fiber bundles, where each bundle is comprised of collagen fibrils. Collagen fibers have been shown to exhibit linear birefringence.

For IPA of 140° the DoCP image-maps (FIG. 27) indicate several features of the rat-tail structure. The outer edges of the tail were highlighted by bright pixels, as were regions of tendon on either side of the central axis along the length of the rat tail leaving a thin sliver of darker pixels between. For IPA of 50°, the outer edges of the tail were also highlighted by bright pixels. However, rather than the inner regions of the tendon being bright, in this case, the regions of the tendon located towards the periphery of the rat-tail were bright, In both DoCP image-maps, there were the common characteristics of dark pixels at the central axis of soft tissue along the length of the tail and the dark bands that cross the tail width-wise.

These results indicate that by using Stokes polarimetry imaging, the IPAs, tissue orientation angle, and geometry of the tissue with respect to the polarized light source contribute to the characterization of tissue in DoLP and DoCP image-maps. One must recognize that the polarization of remitted light is not only influenced by the superficial tissue layers but also by the underlying tissue layers. Hence, this imaging technique provides utility in subsurface tissue imaging.

The foregoing description and drawings merely explain and illustrate the invention and the invention is not limited thereto. While the specification in this invention is described in relation to certain implementation or embodiments, many details are set forth for the purpose of illustration. Thus, the foregoing merely illustrates the principles of the invention. For example, the invention may have other specific forms without departing for its spirit or essential characteristic. The described arrangements are illustrative and not restrictive. To those skilled in the art, the invention is susceptible to additional implementations or embodiments and certain of these details described in this application may be varied considerably without departing from the basic principles of the invention. It will thus be appreciated that those skilled in the art will be able to devise various arrangements which, although not explicitly described or shown herein, embody the principles of the invention and, thus, within its scope and spirit.

What is claimed is:

1. A method of visually quantifying a test material using an imaging system comprising:
   (a) illuminating a portion of the test material at a known angle of incidence with diffuse light of a known and adjustable polarization state;
   (b) receiving light from the test material, the light having a polarization state modified by the test material;
   (c) measuring an intensity of the polarization components of the light received from the test material for each illuminated pixel substantially simultaneously;
   (d) calculating a polarization based parameter in two dimensions for each illuminated pixel; and
   (e) creating an image map for the known and adjustable polarization state with values for each illuminated pixel.

2. The method according to claim 1 further comprising:
   (f) saving the image map for the known and adjustable polarization state;
   (g) varying one parameter of the known and adjustable polarization state of the diffuse light; and
   (h) repeating (a) through (g) for another variation of the known and adjustable polarization state until all desired variations have been applied.

3. The method according to claim 2 further comprising:
   (i) saving the image map for the known angle of incidence;
   (j) changing the known angle of incidence to a new known angle of incidence; and
   (k) repeating (a) through (k) for the new known angle of incidence for each pair of new known angle of incidence and known polarization state desired.

4. The method according to claim 3 further comprising gathering the saved image maps into a movie.

5. The method according to claim 2 wherein each of the values for the image map are one type of polarization based parameter selected from the group comprising azimuth, ellipticity, eccentricity, degree of circular polarization (DoCP), degree of linear polarization (DoLP), degree of total polarization (DoTP), the Stokes vector Q, the Stokes vector U, the Stokes vector V, and any combinations thereof.

6. The method according to claim 5 wherein the adjustable polarization state is varied by moving the diffuse light.

7. The method according to claim 5 wherein the adjustable polarization state is varied by moving the test material.

8. The method according to claim 2 further comprising:
   (i) saving the image map for the known and adjustable polarization state;
   (j) changing the wavelength of the diffuse light; and
   (k) repeating (a) through (k) for another variation of the wavelength of the diffuse light until all desired variations have been applied.

9. The method according to claim 1 further comprising:
   (f) saving the image map for the known angle of incidence;
   (g) changing the known angle of incidence to a new known angle of incidence; and
   (h) repeating (a) through (g) for the new known angle of incidence for each new known angle of incidence desired.

10. The method according to claim 1 further comprising:
    (i) saving the image map for the known and adjustable polarization state;
    (j) changing the wavelength of the diffuse light; and
    (k) repeating (a) through (e) and (i) through (k) for another variation of the wavelength of the diffuse light until all desired variations have been applied.

11. An imaging system for visually quantifying a test material comprising:
    a light source emitting diffuse light of a known polarization state, the diffuse light directed at a known angle of incidence to the test material;
    optics positioned to receive light remitted by the test material, the remitted light having a plurality of constituent waves each having a polarization state modified by the test material;
    a plurality of imaging pixels arranged in a 2-dimensional array, the plurality of imaging pixels being positioned to receive the remitted light from the optics;
    means for substantially simultaneously measuring an intensity of the polarization state of the plurality of constituent waves in the remitted light falling incident on the plurality of imaging pixels;
    means for calculating a polarization based parameter in two dimensions for each of the plurality of imaging pixels; and
    means for creating an image map for the known polarization state with values for each illuminated imaging pixel.

12. The imaging system according to claim 11 further comprising:
    image map storage; and
    a polarization state controller that varies the polarization state of the diffuse light.

13. The imaging system according to claim 12 further comprising a system for changing the angle of known angle of incidence to the test material.

14. The apparatus according to claim 11 further comprising means for gathering the image maps into a movie.

15. The apparatus according to claim 11 wherein each of the values for the image map are one type of polarization based parameter selected from the group comprising azimuth, ellipticity, eccentricity, degree of circular polarization (DoCP), degree of linear polarization (DoLP), degree of total polarization (DoTP), the Stokes vector Q, the Stokes vector U, the Stokes vector V, and any combinations thereof.

16. The apparatus according to claim 11 wherein the optics include a lens, filter, beam splitter, polarizers, waveplates, and mirrors.

17. The apparatus according to claim 16 wherein the optics are associated with a minimally invasive medical device selected from the group comprising a laparoscope, a cyctoscope, an ureteroscope, an arthroscope, and a dermascope.

18. The apparatus according to claim 11 wherein the plurality of imaging pixels are elements of a CCD camera.

19. The apparatus according to claim 11 wherein the plurality of imaging pixels are elements of a CMOS imaging system.

20. The apparatus according to claim 11 wherein the light source has a selectively adjustable wavelength.

* * * * *